(12) United States Patent
Kim et al.

(10) Patent No.: US 11,406,260 B2
(45) Date of Patent: Aug. 9, 2022

(54) MEASUREMENT AND CORRECTION OF HIGH-ORDER OPTICAL ABERRATIONS FOR AN EYE WEARING A CONTACT LENS

(71) Applicant: Ovitz Corporation, Rochester, NY (US)

(72) Inventors: Joung Yoon Kim, Seoul (KR); Nicolas Scott Brown, Rochester, NY (US)

(73) Assignee: Ovitz Corporation, Rochester, NY (US)

(*) Notice: Subject to any disclaimer, the term of this patent is extended or adjusted under 35 U.S.C. 154(b) by 299 days.

(21) Appl. No.: 16/652,585

(22) PCT Filed: Sep. 2, 2019

(86) PCT No.: PCT/US2019/049260
§ 371 (c)(1),
(2) Date: Mar. 31, 2020

(87) PCT Pub. No.: WO2020/047528
PCT Pub. Date: Mar. 5, 2020

(65) Prior Publication Data
US 2020/0237215 A1  Jul. 30, 2020

Related U.S. Application Data

(60) Provisional application No. 62/725,305, filed on Aug. 31, 2018.

(51) Int. Cl.
*A61B 3/14* (2006.01)
*A61B 3/10* (2006.01)
*A61B 3/00* (2006.01)

(52) U.S. Cl.
CPC .......... *A61B 3/1015* (2013.01); *A61B 3/0025* (2013.01); *A61B 3/14* (2013.01)

(58) Field of Classification Search
CPC ....... A61B 3/0025; A61B 3/10; A61B 3/1015; A61B 3/103; A61B 3/14; G02C 7/04; G02C 2202/22
See application file for complete search history.

(56) References Cited

U.S. PATENT DOCUMENTS 5,953,098 A   9/1999   Lieberman et al.
6,050,687 A   4/2000   Bille et al.
(Continued)

FOREIGN PATENT DOCUMENTS

WO   WO02/088830 A1    11/2002
WO   WO2008/010977 A1   1/2008

OTHER PUBLICATIONS

Ovitz Corporation, PCT/US19/49260, International Search Report and Written Opinion, dated Jan. 10, 2020, 13 pgs.
(Continued)

*Primary Examiner* — Jack Dinh
(74) *Attorney, Agent, or Firm* — Morgan, Lewis & Bockius LLP

(57) ABSTRACT

Devices and methods for measuring high order aberrations from an eye are described. A method includes obtaining information indicating one or more aberrations of an eye, and obtaining information indicating one or more of a visual axis of the eye, a center of a pupil of the eye, and a corneal vertex of the eye. The information from the optical device is used to modify a design of a contact lens so that a combination of the eye and the modified contact lens has reduced high order aberrations. In some cases, information indicating the orientation of the contact lens positioned on the eye is also used. The optical device may include an aberrometer; a first light source for providing first light toward an eye; a
(Continued)

lens assembly for collecting light from the eye; and a first image sensor for receiving light that has been transmitted through the lens assembly.

1 Claim, 21 Drawing Sheets

(56) References Cited

U.S. PATENT DOCUMENTS

| | | |
|---|---|---|
| 8,623,001 B2 | 1/2014 | Preuss et al. |
| 9,022,570 B2 | 5/2015 | Applegate et al. |
| 9,427,156 B1 | 8/2016 | Steven et al. |
| 9,658,470 B2 | 5/2017 | Applegate et al. |
| 2006/0028619 A1 | 2/2006 | Fujieda et al. |
| 2007/0273828 A1 | 11/2007 | Polland et al. |
| 2009/0161090 A1 | 6/2009 | Campbell et al. |
| 2011/0273669 A1 | 11/2011 | Abitbol et al. |
| 2012/0257166 A1 | 10/2012 | Francis et al. |
| 2013/0345806 A1 | 12/2013 | Piers et al. |
| 2014/0176900 A1 | 6/2014 | Applegate et al. |
| 2018/0125355 A1 | 5/2018 | Mrochen et al. |
| 2018/0164535 A1 | 6/2018 | Brown |

OTHER PUBLICATIONS

Kim, Office Action, U.S. Appl. No. 16/558,298, dated Jun. 16, 2021, 12 pgs.
Kim, Office Action, U.S. Appl. No. 16/558,298, dated Dec. 7, 2021, 7 pgs.
Ovitz Corporation, Extended European Search Report, EP19854103.9, dated May 25, 2022, 8 pgs.
Kim, Notice of Allowance, U.S. Appl. No. 16/558,298, dated Apr. 1, 2022, 8 pgs.

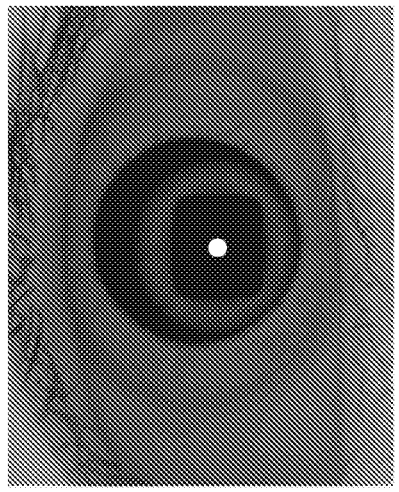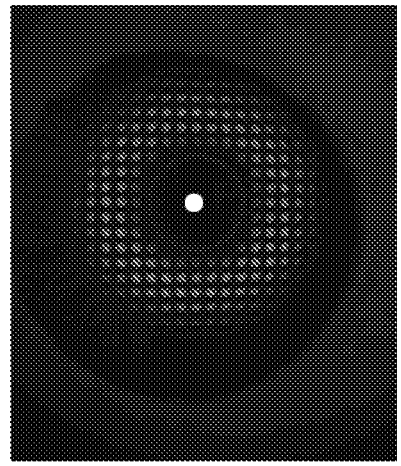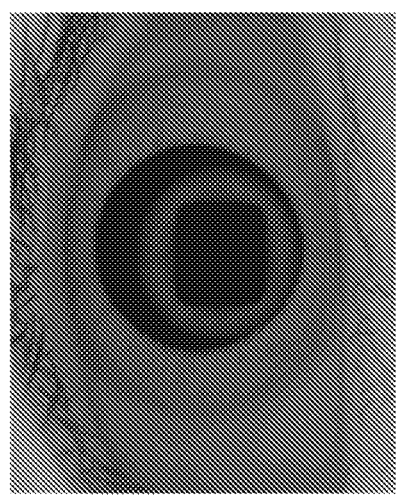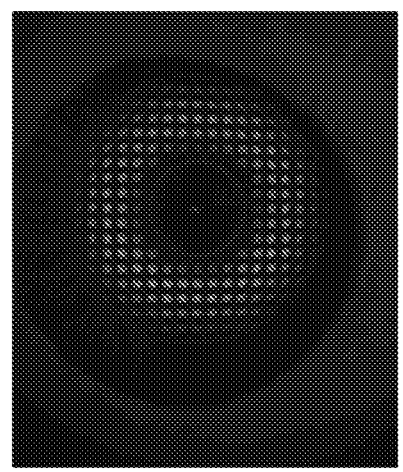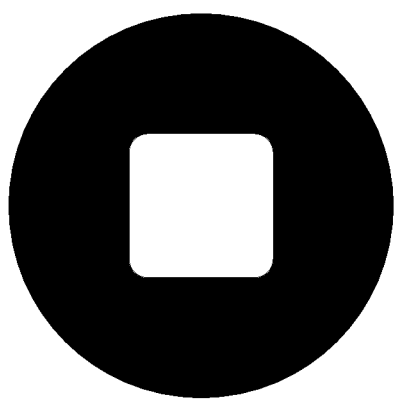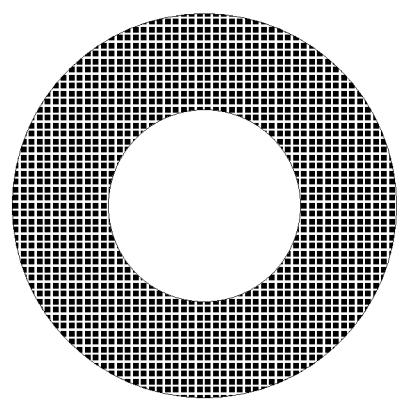
Figure 4A
Figure 4B

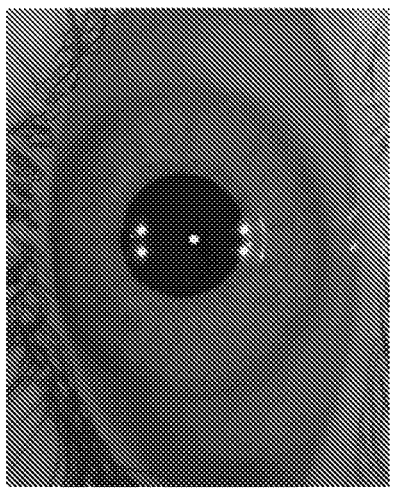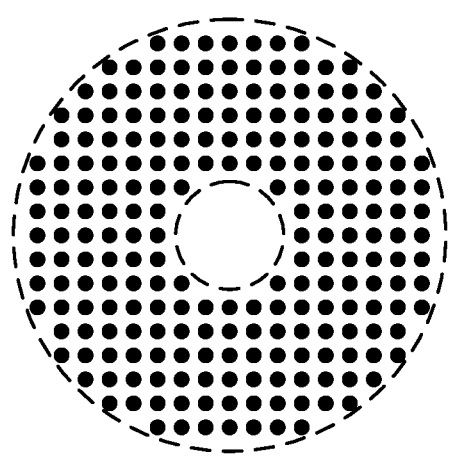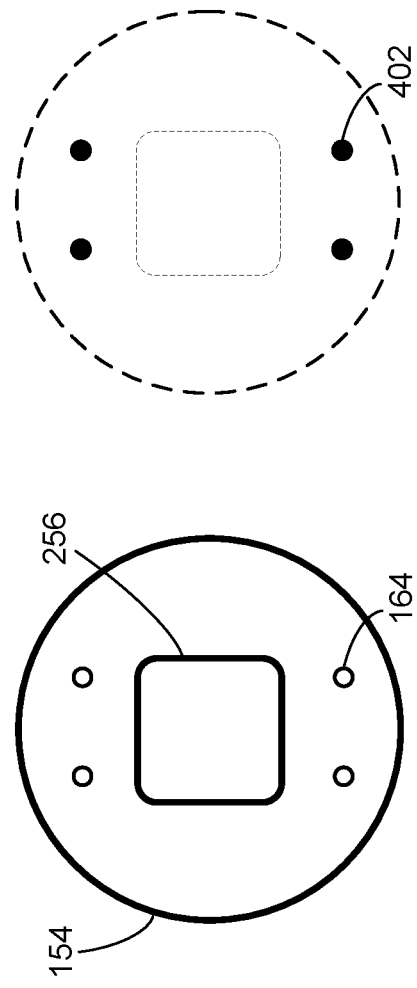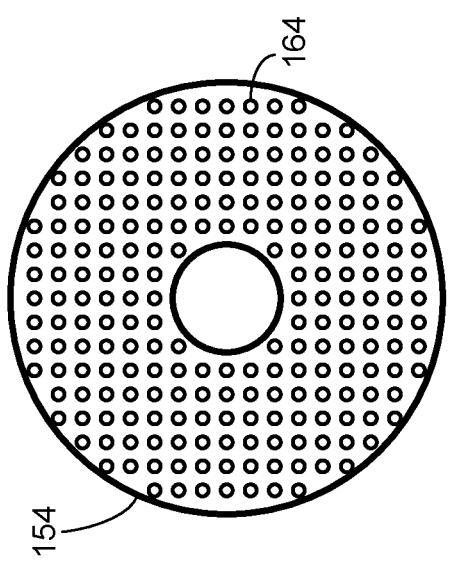
Figure 4C
Figure 4D

700

702 Determine one or more aberrations of a combination of an eye and a contact lens positioned adjacent to the eye and determine a location of a center of the contact lens by using a single optical device

704 Determine the one or more aberrations of the combination of the eye and the contact lens based on information corresponding to the light received by the first image sensor; and determine the location of the center of the contact lens based on information corresponding to the light received by the second image sensor

706 Concurrently transfer the first light emitted from the first light source toward the combination of the eye and the contact lens while transferring the second light emitted from the second light source toward the combination of the eye and the contact lens

708 Project an image of a reference toward the eye concurrently with transferring the first light emitted from the first light source toward the combination of the eye and the contact lens and transferring the second light emitted from the second light source toward the combination of the eye and the contact lens

710 Concurrently receive light with the first image sensor while receiving light with the second image sensor

712 Sequentially transfer the first light emitted from the first light source toward the combination of the eye and the contact lens and transfer the second light emitted from the second light source toward the combination of the eye and the contact lens

714 Sequentially receive light with the first image sensor and receive light with the second image sensor

716 Store information representing the light received by the first image sensor; and store information representing the light received by the second image sensor in conjunction with the information representing the light received by the first image sensor

718 Store information representing the light received by the first image sensor; and store information representing the location of the center of the contact lens in conjunction with the information representing the light received by the first image sensor

Figure 7

MEASUREMENT AND CORRECTION OF HIGH-ORDER OPTICAL ABERRATIONS FOR AN EYE WEARING A CONTACT LENS

CROSS REFERENCE TO RELATED APPLICATIONS

This Application is a United States National Stage Application filed under 35 U.S.C. § 371 of PCT Patent Application Serial No. PCT/US2019/049260 filed on Sep. 2, 2019, which claims the benefit of and priority to U.S. Provisional Patent Application No. 62/725,305 filed on Aug. 31, 2018. This application is also related to U.S. patent application Ser. No. 16/558,298 filed Sep. 2, 2019. All of these applications are incorporated by reference in their entirety.

TECHNICAL FIELD

This application relates generally to measuring high-order optical aberrations for an eye wearing a contact lens and making individualized contact lenses based on the measurements.

BACKGROUND

Eyes are important organs, which play a critical role in human's visual perception. An eye has a roughly spherical shape and includes multiple elements, such as cornea, lens, vitreous humour, and retina. Imperfections in these components can cause reduction or loss of vision. For example, too much or too little optical power in the eye can lead to blurring of the vision (e.g., near-sightedness or far-sightedness), and astigmatism can also cause blurring of the vision.

Corrective lenses (e.g., glasses and contact lenses) are frequently used to compensate for blurring caused by too much or too little optical power and/or astigmatism. However, when eyes have high-order aberrations (e.g., aberrations higher than astigmatism in the Zernike polynomial model of aberrations), conventional corrective lenses cannot adequately compensate for all of the aberrations associated with the eyes, resulting in blurry images even when corrective lenses are used.

SUMMARY

Accordingly, there is a need for corrective lenses that can compensate for high-order aberrations and methods and devices that can accurately measure high-order aberrations so that proper corrective lenses can be designed and/or made.

The above deficiencies and other problems associated with conventional devices and corresponding methods are reduced or eliminated by the disclosed devices and methods.

As described in more detail below, some embodiments involve a method that includes obtaining, with an optical device, information indicating one or more aberrations of an eye; and obtaining, with the optical device, information indicating one or more of a visual axis of the eye, a center of a pupil of the eye, and a corneal vertex of the eye.

Also described is an optical device including an aberrometer; a first light source for providing first light toward an eye; a lens assembly for collecting light from the eye; and a first image sensor for receiving light that has been transmitted through the lens assembly.

In accordance with some embodiments, a method for making a personalized contact lens includes selecting a surface profile based on (i) one or more aberrations of an eye and (ii) a position of a contact lens relative to one or more of a visual axis of the eye, a center of a pupil of the eye, and a corneal vertex of the eye; and fabricating a contact lens having the selected surface profile. Some embodiments include a contact lens made by any method described herein.

In accordance with some embodiments, a method for making a personalized multifocal lens includes selecting a surface profile based on (i) one or more aberrations of an eye and (ii) a position of a contact lens relative to one or more of a visual axis of the eye, a center of a pupil of the eye, and a corneal vertex of the eye. An optical zone of the surface profile is positioned based on the position of the contact lens relative to the visual axis of the eye. The surface profile includes a first region corresponding to a first optical power and a second region corresponding a second optical power that is different from the first optical power. The method also includes fabricating a contact lens having the selected surface profile. Some embodiments include a multifocal contact lens made by any method described herein.

In accordance with some embodiments, a method includes determining one or more aberrations of a combination of an eye and a contact lens positioned adjacent to the eye, and determining a location of a center of the contact lens by using a single optical device. The single optical device includes a lens assembly; and a wavefront sensor that includes: a first light source configured to emit first light and transfer the first light emitted from the first light source toward the combination of the eye and the contact lens; the lens assembly for collecting light from the combination of the eye and the contact lens; an array of lenses that is distinct from the lens assembly, the array of lenses configured to focus light transmitted through the lens assembly; and a first image sensor configured to receive light, from the combination of the eye and the contact lens, transmitted through the lens assembly and the array of lenses. The single optical device also includes a contact lens center sensor that includes: a second light source configured to emit second light and transfer the second light emitted from the second light source toward the combination of the eye and the contact lens; the lens assembly for collecting light from the combination of the eye and the contact lens; one or more lenses configured to focus light transmitted through the lens assembly, the one or more lenses being distinct and separate from the array of lenses; and a second image sensor configured to receive light, from the combination of the eye and the contact lens, transmitted through the lens assembly and the one or more lenses.

In accordance with some embodiments, a method includes transferring first light from a first light source toward a combination of an eye and a contact lens positioned adjacent to the eye; receiving, with a first image sensor, light from the combination of the eye and the contact lens, transmitted through a lens assembly and an array of lenses; determining one or more aberrations of the combination of the eye and the contact lens; transferring second light from a second light source toward the combination of the eye and the contact lens; receiving, with a second image sensor distinct and separate from the first image sensor, light from the combination of the eye and the contact lens, transmitted through the lens assembly and one or more lenses; and determining a location of a center of the contact lens.

In accordance with some embodiments, an optical device includes a lens assembly; and a wavefront sensor that includes: a first light source configured to emit first light and transfer the first light emitted from the first light source toward a combination of an eye and a contact lens positioned adjacent to the eye; the lens assembly for collecting light from the combination of the eye and the contact lens; an array of lenses that is distinct from the lens assembly, the array of lenses configured to focus light transmitted through the lens assembly; and a first image sensor configured to receive light, from the combination of the eye and the contact lens, transmitted through the lens assembly and the array of lenses. The optical device also includes a contact lens center sensor that includes: a second light source configured to emit second light and transfer the second light emitted from the second light source toward the combination of the eye and the contact lens; the lens assembly for collecting light from the combination of the eye and the contact lens; one or more lenses configured to focus light transmitted through the lens assembly, the one or more lenses being distinct and separate from the array of lenses; and a second image sensor configured to receive light, from the combination of the eye and the contact lens, transmitted through the lens assembly and the one or more lenses. The optical device also includes one or more processors; and memory storing one or more programs for execution by the one or more processors, the one or more programs including instructions for: determining one or more aberrations of the combination of the eye and the contact lens based on information corresponding to the light received by the first image sensor; and determining a location of a center of the contact lens based on information corresponding to the light received by the second image sensor.

In accordance with some embodiments, a method for making a contact lens includes selecting a surface profile based on (i) one or more aberrations of a combination of an eye and a contact lens positioned adjacent to the eye and (ii) a location of a center of the contact lens; and making a lens having the selected surface profile.

In accordance with some embodiments, a corrective lens (e.g., a contact lens) is made by any method described herein.

Thus, devices are provided with more efficient and accurate methods for performing wavefront sensing and determining vertices of contact lenses, thereby increasing the effectiveness, efficiency, accuracy, and user satisfaction with such devices. Such devices and corresponding methods may complement or replace conventional methods for performing wavefront sensing.

BRIEF DESCRIPTION OF THE DRAWINGS

For a better understanding of the various described embodiments, reference should be made to the Description of Embodiments below, in conjunction with the following drawings in which like reference numerals refer to corresponding parts throughout the figures.

FIGS. 4A and 4B illustrates example illumination patterns, their projection on eyes, and determination of contact lens vertices in accordance with some embodiments.

FIGS. 4C and 4D illustrate example light sources in accordance with some embodiments.

FIG. 7 is a flowchart representing a method of optical measurements with an optical device, in accordance with some embodiments.

DESCRIPTION OF EMBODIMENTS

Figure 1A:
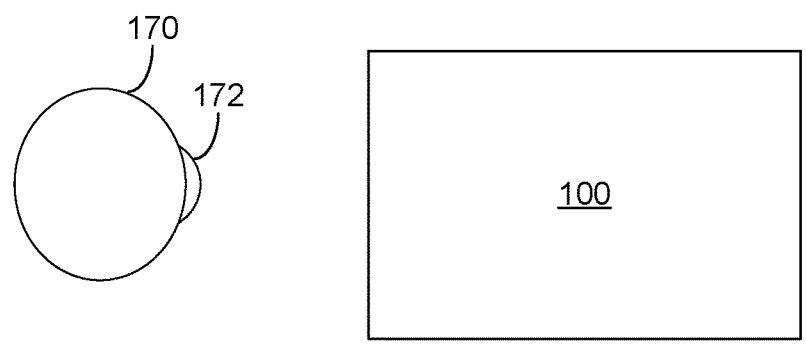
FIG. 1A illustrates measurement of aberrations from an eye in accordance with some embodiments.

Reference will be made to embodiments, examples of which are illustrated in the accompanying drawings. In the following description, numerous specific details are set forth in order to provide a thorough understanding of the various described embodiments. However, it will be apparent to one of ordinary skill in the art that the various described embodiments may be practiced without these particular details. In other instances, methods, procedures, components, circuits, and networks that are well-known to those of ordinary skill in the art are not described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first image sensor could be termed a second image sensor, and, similarly, a second image sensor could be termed a first image sensor, without departing from the scope of the various described embodiments. The first image sensor and the second image sensor are both image sensors, but they are not the same image sensor.

The terminology used in the description of the embodiments herein is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting (the stated condition or event)" or "in response to detecting (the stated condition or event)," depending on the context.

A lens designed to compensate for high-order aberrations of an eye needs accurate positioning on an eye. If a lens designed to compensate for high-order aberrations of an eye is not placed accurately, the lens may not be effective in compensating for high-order aberrations of the eye and may even exacerbate the high-order aberrations.

One of the additional challenges is that that when a contact lens is used to compensate for high-order aberrations of an eye, an apex of a contact lens is not necessarily positioned on a visual axis of the eye. Thus, a relative position between the visual axis of the eye and the contact lens needs to be reflected in the design of the contact lens, which in turn, requires accurate measurements of the visual axis of the eye and a position of the contact lens on the eye. The visual axis of the eye is often believed to be located adjacent to a center of a pupil, and thus, the center of a pupil is often used as an approximation of the visual axis of the eye. However, the error in such approximation may hamper the performance of a contact lens designed to compensate for high-order aberrations. Thus, for designing a contact lens that can compensate for the high-order aberrations, an accurate measurement of the visual axis of the eye may be necessary in some cases.

FIG. 1A is a schematic diagram illustrating measurement of aberrations from eye 170 in accordance with some embodiments. Light from optical device 100 (e.g., an aberrometer) is transmitted through cornea 172 and other components of eye 170 (e.g., lens) and returned back to optical device 100, which in turn analyzes the returned light to determine aberrations in eye 170.

Figure 1B:
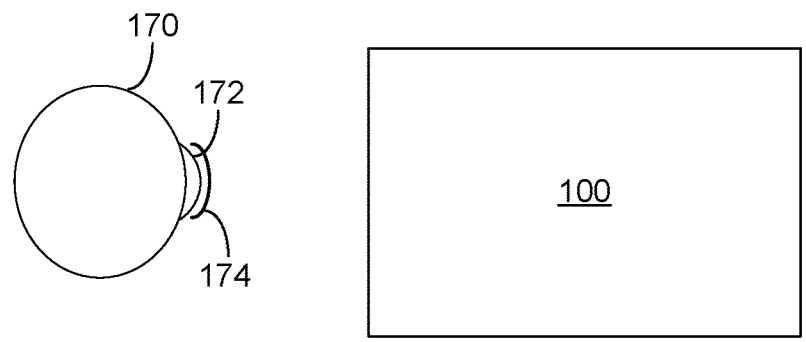
FIG. 1B illustrates measurement of aberrations from a combination of an eye and a contact lens in accordance with some embodiments.

FIG. 1B is a schematic diagram illustrating measurement of aberrations from a combination of an eye and a contact lens in accordance with some embodiments. In order to determine remaining aberrations when contact lens 174 is worn, device 100 measures aberrations while contact lens 174 (e.g., a conventional contact lens that is configured to compensate for optical power and astigmatism) is placed over cornea 172 of eye 170. For example, when contact lens 174 compensates for power and astigmatism in eye 170, optical device 100 may detect only high order aberrations. Also while contact lens 174 is placed on eye 170, the position of contact lens 174 on eye 170 can be measured (e.g., by storing an image of contact lens 174 on eye 170).

Figure 1C:
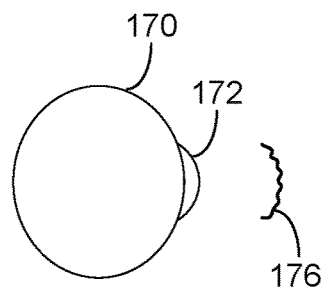
FIG. 1C illustrates a modified contact lens in accordance with some embodiments.

FIG. 1C is a schematic diagram illustrating modified contact lens 176 in accordance with some embodiments. Unlike a conventional contact lens configured to compensate for power and astigmatism only, contact lens 176 configured to compensate for power, astigmatism, and high-order aberration has a complex surface profile. Features of contact lens 176 are exaggerated in FIG. 1C and not drawn to scale.

Figure 1D:
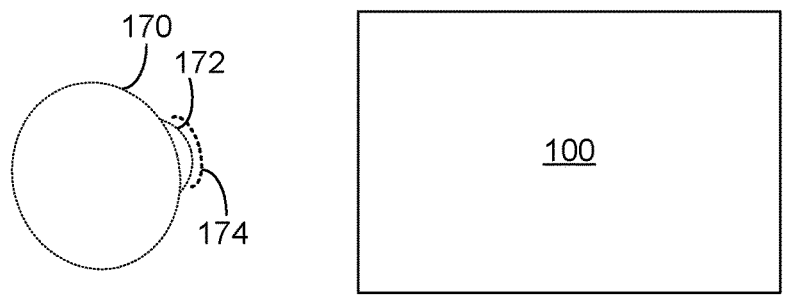
FIG. 1D illustrates measurement of aberrations from an eye in an off-axis position in accordance with some embodiments.

FIG. 1D is a schematic diagram illustrating measurement of aberrations from eye 170 in an off-axis position in accordance with some embodiments. When aberrations are measured from eye 170 in an off-axis position, the measured aberrations may not correspond to aberrations measured from an optical reference axis of eye 170. Thus, a lens that compensates for aberrations measured from eye 170 in an off-axis position may not adequately compensate for aberrations on the optical reference axis of eye 170.

Figure 1E:
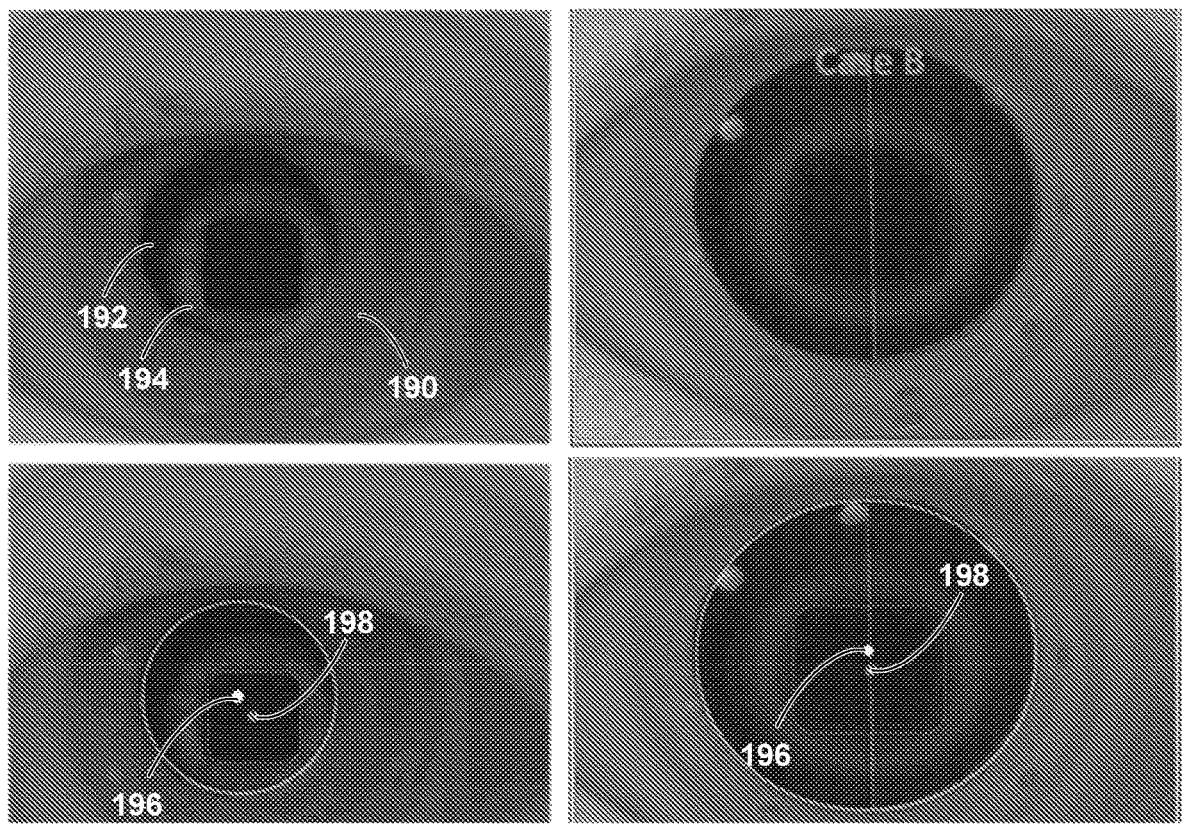
FIG. 1E illustrates offsets between an optical reference axis and a center of a contact lens in accordance with some embodiments.

FIG. 1E illustrates offsets between an optical reference axis (e.g., an axis based on a corneal vertex) of an eye and a center of a pupil in accordance with some embodiments. Images shown in FIG. 1E are collected with a device described with respect to FIGS. 2A and 2B.

The top-left image shows iris 190 and pupil 192 of an eye and reflection 194 of a projected image. The bottom-left image, which includes a markup to the top-left image, shows the center 196 of pupil 192 and a corneal vertex 198 of the eye, which, in FIG. 1E, corresponds to a center of the projected image. In this image, the center 196 of pupil does not match with the corneal vertex 198 of the eye.

The top-right image shows another example of an iris and a pupil of an eye and reflection of a projected image. The bottom-right image, which includes a markup to the top-right image, shows the center 196 of pupil and a corneal vertex 198 of the eye. Similar to the bottom-left image, the center 196 of pupil and the corneal vertex 198 of the eye do not match in the bottom-right image. Thus, a lens designed to correct The offset between the center 196 of pupil and the corneal vertex 198 (e.g., a relative position of the center 196 of pupil and the corneal vertex 198) and/or the offset between the corneal vertex 198 and a center of a contact lens can be used to design (or modify a design of) a corrective lens, such as a contact lens. Design of a corrective lens typically includes determining a surface profile (e.g., a curvature and a thickness profile) of the corrective lens.

Figure 1F:
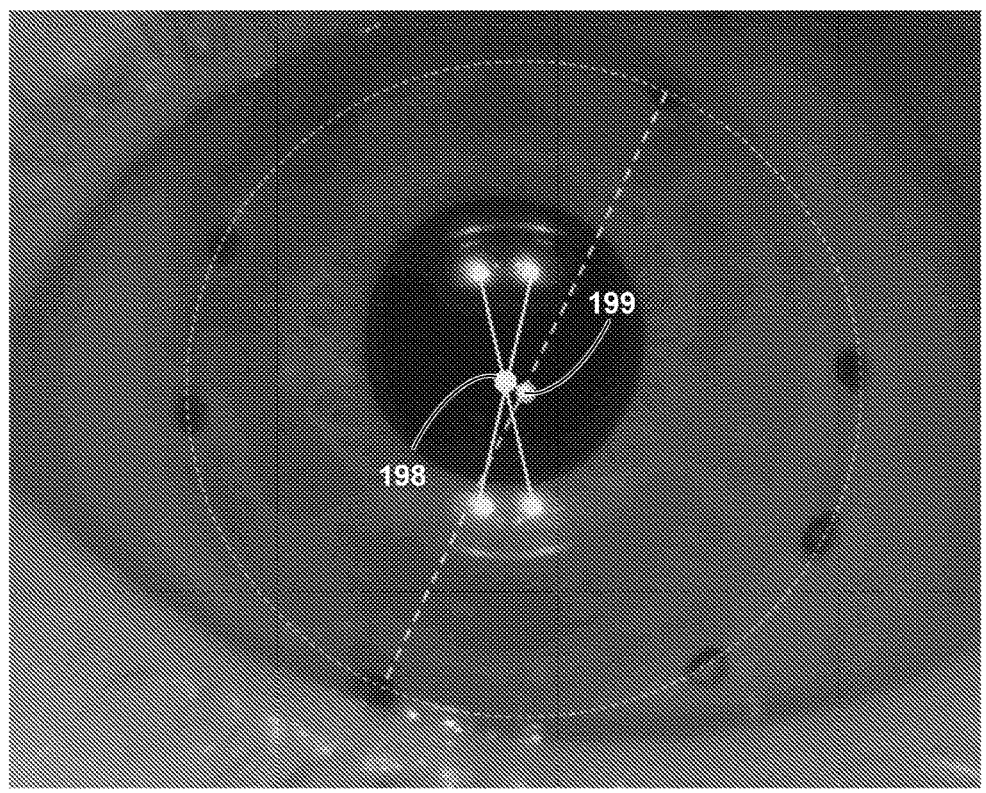
FIGS. 1F and 1G illustrate offset among an optical reference axis of an eye, a center of a contact lens, and a center of a pupil in accordance with some embodiments.

FIG. 1F illustrates offset between an optical reference axis (e.g., an axis based on a corneal vertex) of an eye and a center (or a vertex) of a contact lens in accordance with some embodiments. The contact lens shown in FIG. 1F has markers around its periphery, and based on positions of the markers, a center 199 of the contact lens can be determined. In some embodiments, the corneal vertex 198 is determined based on subject-fixated coaxially sighted light reflex. In some embodiments, the subject-fixated coaxially sighted light reflex is a subject-fixated coaxially sighted corneal light reflex (e.g., light reflected by a corneal surface, such as an anterior corneal surface) or a subject-fixated coaxially sighted contact lens light reflex (e.g., light reflected by a surface of a contact lens, such as an anterior contact lens surface). Based on a pattern of light illuminating the eye, a corneal vertex 198 of the eye can be determined. By utilizing such information, a surface profile for correcting high-order aberrations can be placed based on the location of the corneal vertex 198 of the eye.

Figure 1G:
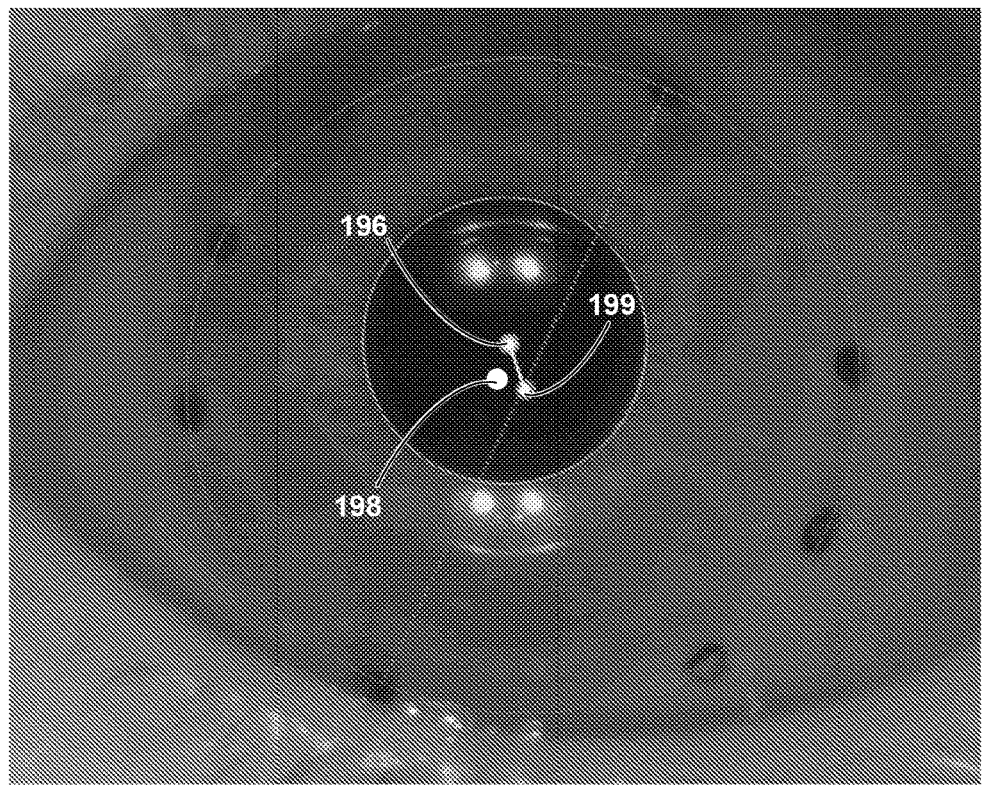

FIG. 1G is similar to FIG. 1F except that a center 196 of the pupil is annotated to illustrate offsets among the corneal vertex 198 of the eye, the center 199 of the contact lens, and the center 196 of the pupil. FIG. 1G shows the offset between the center 196 of the pupil and the corneal vertex 198 of the eye. A contact lens for which the surface profile for correcting high-order aberrations is positioned based on the location of the center 196 of the pupil is ineffective in correcting high-order aberrations.

Figure 1H:
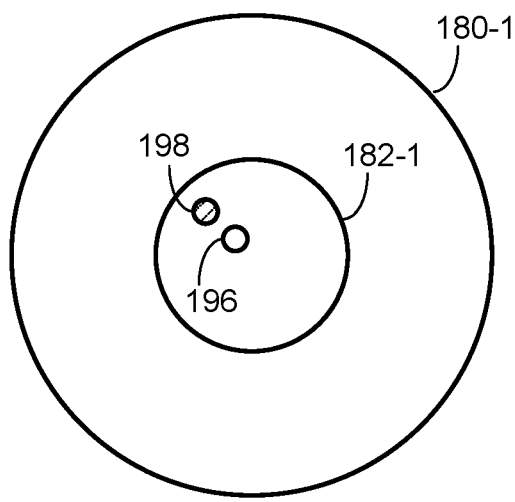
FIGS. 1H-1J are schematic diagrams illustrating correction of a decentered optical zone in accordance with some embodiments.
Figure 1I:
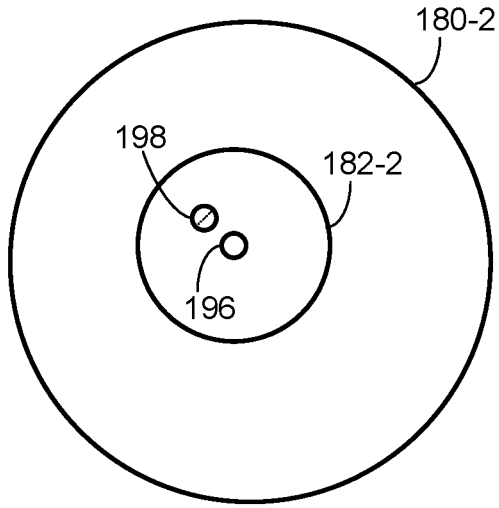
Figure 1J:
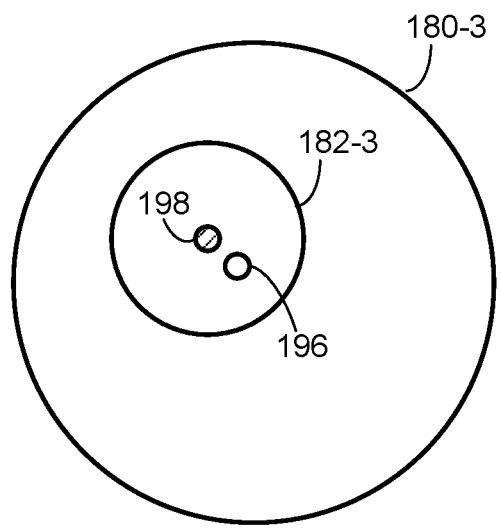

FIGS. 1H-1J are schematic diagrams illustrating correction of a decentered optical zone in accordance with some embodiments. In FIGS. 1H-1J, an optical zone 182 corresponds to a region less than the entire surface of a contact lens 180 (e.g., contact lens 180-1, 180-2, or 180-3). However, in some embodiments, the optical zone 182 corresponds to the entire surface of the contact lens 180.

FIG. 1H illustrates a contact lens 180-1 with an optical zone 182-1, a center 196 of the pupil, and a corneal vertex 198 of the eye. In FIG. 1H, the optical zone 182-1 is located in the middle of the contact lens 180-1.

FIG. 1I illustrates a contact lens 180-2 with an optical zone 182-2 centered around the center 196 of the pupil.

FIG. 1J illustrates a contact lens 180-3 with an optical zone 182-3 centered around the corneal vertex 198 of the eye. When a surface profile for correcting high-order aberrations is positioned around the corneal vertex 198 of the eye, the high-order aberrations can be effectively reduced or eliminated.

FIGS. 1K-1N are schematic diagrams illustrating correction of high-order aberrations in accordance with some embodiments.

Figure 1K:
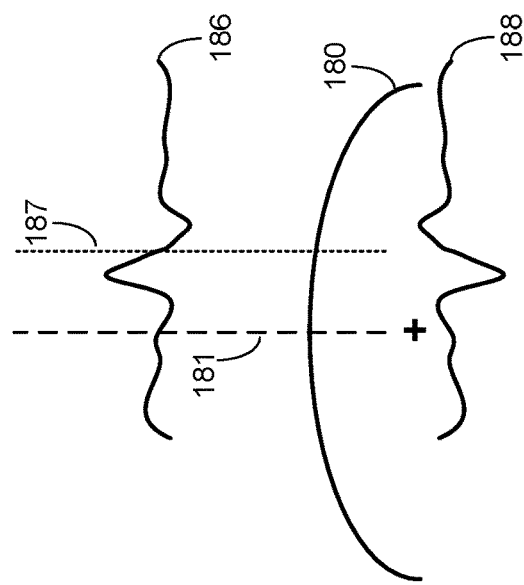
FIGS. 1K-1N are schematic diagrams illustrating correction of high-order aberrations in accordance with some embodiments.

FIG. 1K illustrates a surface profile of a contact lens 180 without high-order correction. As a result, an eye wearing the contact lens 180 may see high-order aberrations represented by line 186. The visual axis 187 of the eye is typically not aligned with the centerline 181 of the contact lens 180, and thus, the measured high-order aberrations are not aligned with the center of the contact lens 180.

Figure 1L:
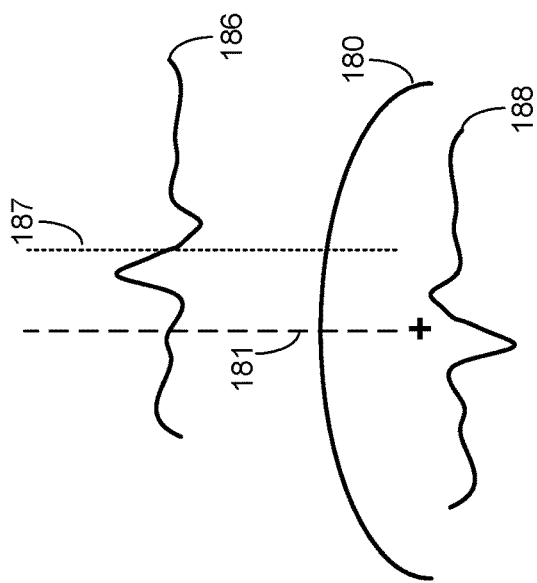

FIG. 1L illustrates modification of the surface profile of the contact lens 180 by superposing a surface profile 188 configured to compensate for the high-order aberrations. However, when the surface profile 188 is positioned around the centerline 181 of the contact lens 180 as shown in FIG. 1L, the combined surface profile is not effective in reducing the high-order aberrations, as the surface profile 188 is offset from the high-order aberrations measured along the visual axis 187 of the eye.

Figure 1M:
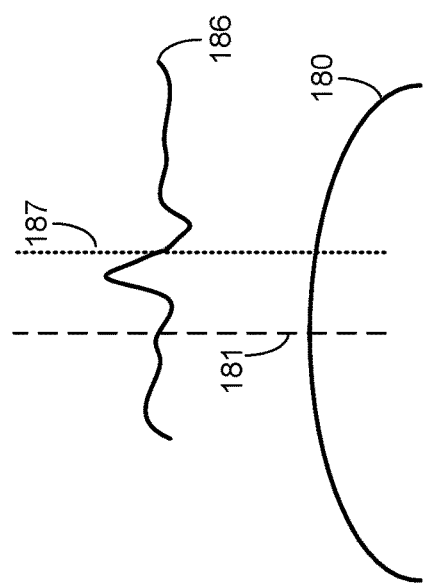

FIG. 1M illustrates modification of the surface profile of the contact lens 180 by superposing the surface profile 188 configured to compensate for the high-order aberrations where the surface profile 188 is positioned around the visual axis 187 of the eye instead of the centerline 181 of the contact lens 180.

Figure 1N:
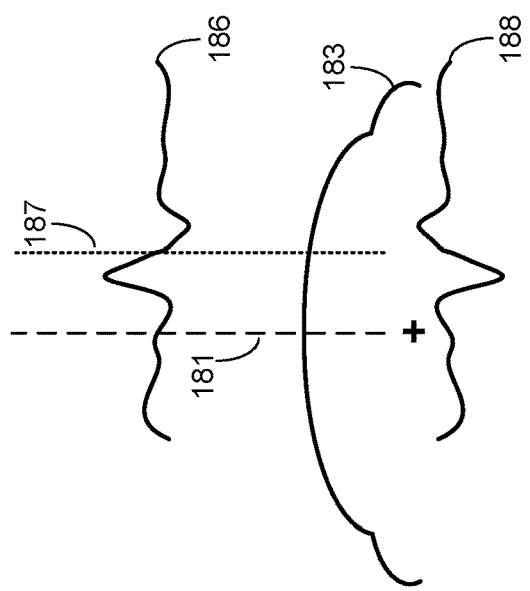

FIG. 1N is similar to FIG. 1M except that the modification of the surface profile can be applied to a multifocal lens 183.

FIGS. 1O-1R illustrate correction of an orientation of a contact lens.

Figure 1O:
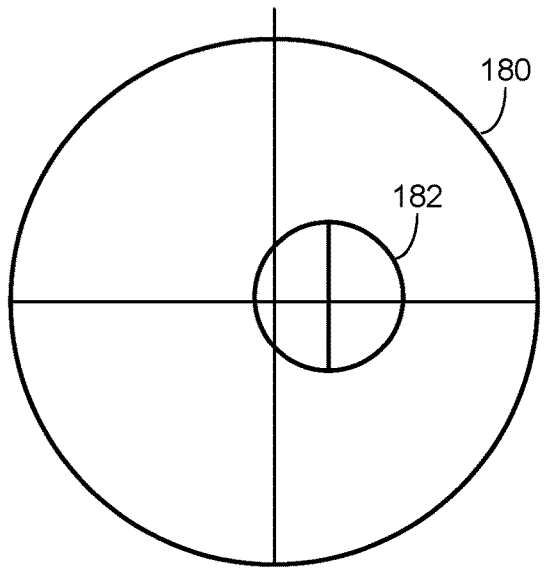
FIGS. 1O-1R illustrate correction of an orientation of a contact lens.
Figure 1P:
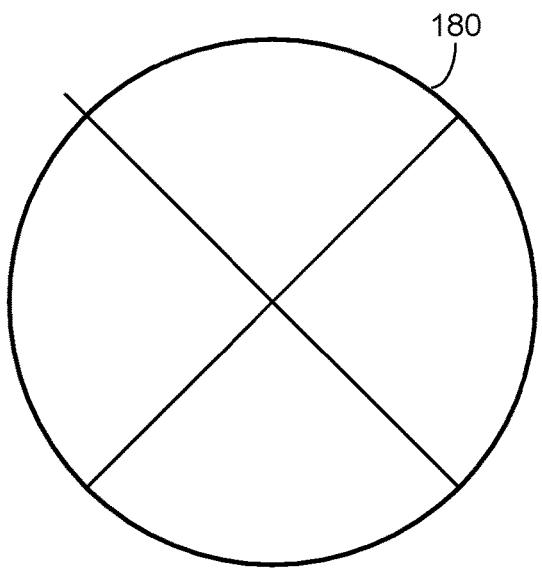
Figure 1Q:
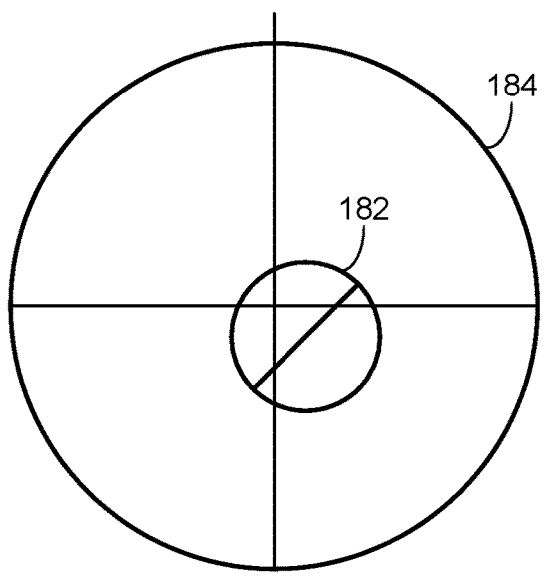
Figure 1R:
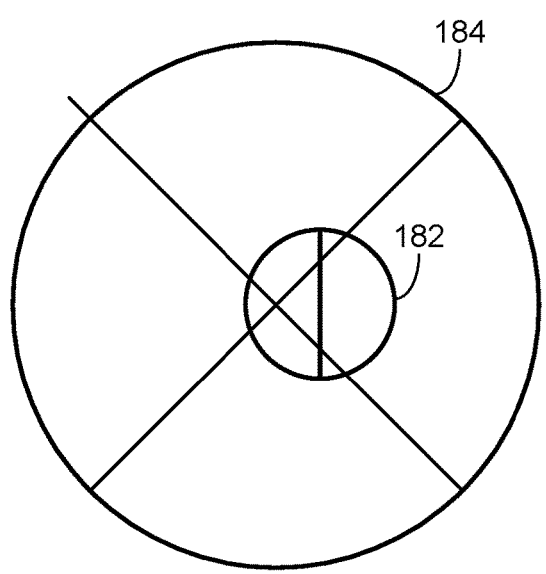

FIG. 1O illustrates a contact lens 180 and an optical zone 182 containing a surface profile for correcting aberrations (including high-order aberrations) of an eye. However, if it is determined that the contact lens 180 will change its orientation once placed on the eye as illustrated in FIG. 1P, modification of the surface profile (or a modification of the position and the orientation of the optical zone 182) is necessary, as shown in FIG. 1Q. In FIG. 1Q, the position and the orientation of the optical zone 182 are modified so that once the contact lens 184 corresponding to the modified surface profile is placed on the eye, the optical zone 182 is located at a position and in an orientation that would correct aberrations (including high-order aberrations) of the eye, as illustrated in FIG. 1R.

FIGS. 1S-1W illustrate example contact lenses made by the methods described herein, in accordance with some embodiments.

Figure 1S:
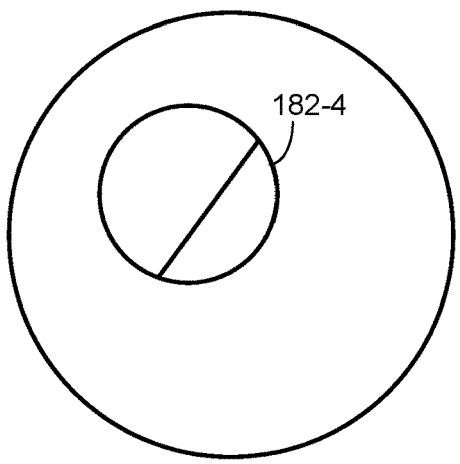
FIGS. 1S-1U illustrate example multifocal contact lenses.
Figure 1T:
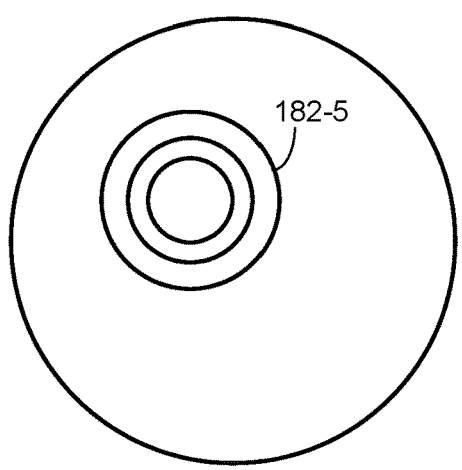
Figure 1U:
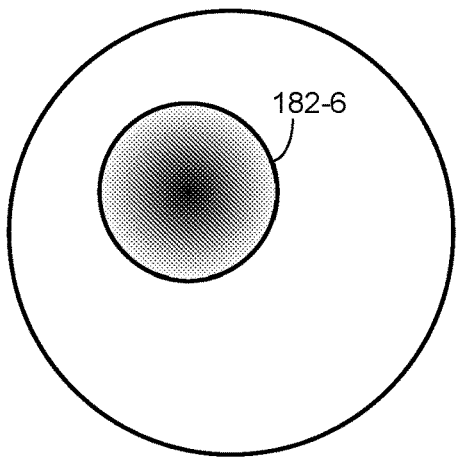

FIGS. 1S-1U illustrate example multifocal contact lenses.

In FIG. 1S, the optical zone 182-4 has two regions: a first region corresponding to a first optical power (e.g., for viewing objects located at a distance) and a second region corresponding to a second optical power different from the first optical power (e.g., for viewing near objects).

In FIG. 1T, the optical zone 182-5 has multiple concentric rings for providing different optical powers for near and distance viewing.

In FIG. 1U, the optical zone 182-6 has an aspheric profile for providing the first optical power in the center region and the second optical power in the surrounding region.

Figure 1V:
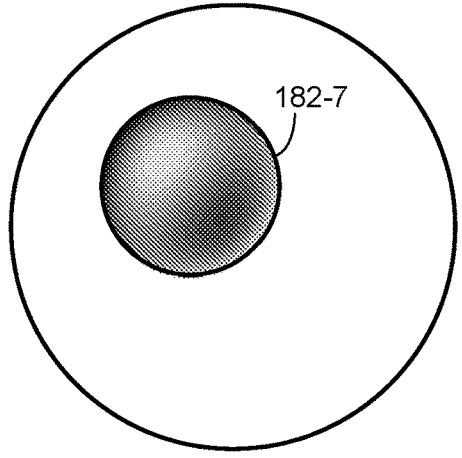
FIG. 1V illustrates a contact lens, in which an optical zone has a surface profile configured for correcting high-order aberrations, in accordance with some embodiments.

FIG. 1V illustrates a contact lens, in which the optical zone 182-7 has a surface profile configured for correcting high-order aberrations.

Figure 1W:
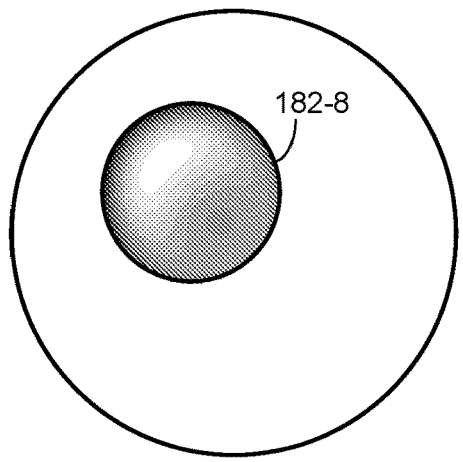
FIG. 1W illustrates a multifocal contact lens, in which an optical zone has a surface profile configured for providing different optical powers in separate zones while correcting high-order aberrations, in accordance with some embodiments.

FIG. 1W illustrates a multifocal contact lens, in which the optical zone 182-8 has a surface profile configured for providing different optical powers in separate zones while correcting high-order aberrations.

The offsetting and reorienting of the surface profile can be described using mathematical equations as explained below.

In some cases, the high-order aberrations measured by device 100 is offset to obtain a modified aberration profile, which is used to modify the design of the corrective lens. This may be described as follows. When changes-in-a-surface-profile $S_C(\theta, \varphi)$ is required to correct for aberrations observed from an eye wearing a contact lens having original surface profile $S_O(\theta, \varphi)$, where $\theta$ is a horizontal angle and $\varphi$ is a vertical angle, the modified surface profile $S_M(\theta, \varphi)$ is as follows:

$$S_M(\theta,\varphi)=S_O(\theta,\varphi)+S_C(\theta,\varphi)$$

However, when the aberrations are observed from a combination of an eye and a contact lens where the center of the contact lens is offset from the center of pupil by horizontal and vertical angles $\theta_0$ and $\varphi_0$, the offset-corrected modified surface profile $S_M(\theta, \varphi)$ is as follows:

$$S_{OCM}(\theta,\varphi)=S_O(\theta,\varphi)+S_C(\theta-\theta_0,\varphi-\varphi_0)$$

As explained above, the offset of the corneal vertex from the center of pupil (or the offset of the center of pupil from the corneal vertex) can play an important role in the lens design. By utilizing the offset-corrected modified surface profile $S_M(\theta, \varphi)$, the aberrations associated with offset position of a contact lens on an eye can be reduced or eliminated.

Similarly, a rotational alignment of a contact lens can also play an important role in the lens design. A contact lens, once placed on an eye, may rotate so that its orientation does not align with a vertical axis across the eye. An offset-and-orientation-corrected modified surface profile $S_{OCM}(\theta, \varphi)$ is as follows:

$$S_{OOCM}(\theta,\varphi)=S_O(\theta,\varphi)+S_C(R_\psi(\theta-\theta_0,\varphi-\varphi_0))$$

where R is a rotation matrix, which can be expressed as $R_\psi$=|cos $\psi$ −sin $\psi$|

|sin $\psi$ cos $\psi$|.

By utilizing the offset-and-orientation-corrected modified surface profile $S_{OOCM}$, the aberrations associated with offset position and rotation of a contact lens on an eye can be reduced or eliminated.

Figure 2A:
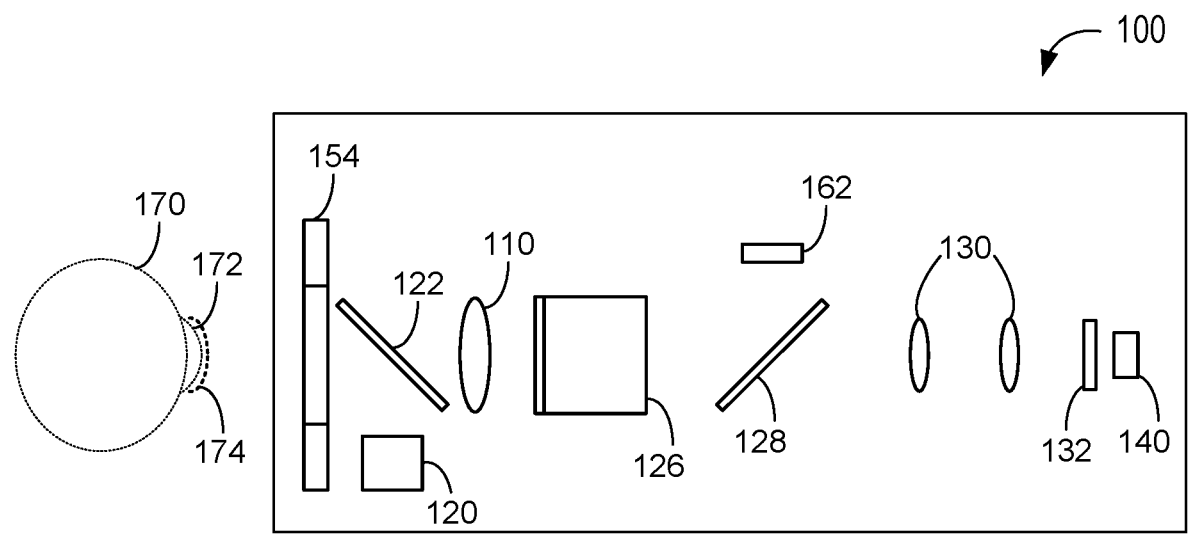
FIGS. 2A and 2B illustrate optical components of an optical device in accordance with some embodiments.
Figure 2B:
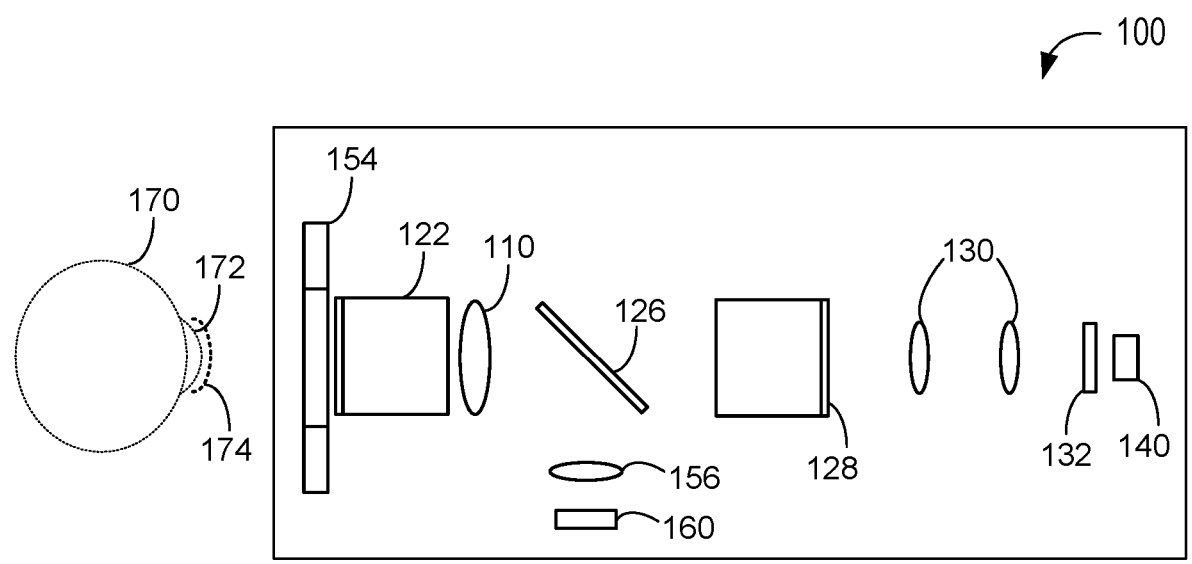

FIGS. 2A and 2B illustrate optical components of optical device 100 in accordance with some embodiments. FIG. 2A is a side view of the optical components of optical device 100, and FIG. 2B is a top view of the optical components of optical device 100. In FIG. 2A, one or more lenses 156 and second image sensor 160 are not shown to avoid obscuring other components of optical device 100 shown in FIG. 2A. In FIG. 2B, pattern 162 is not shown to avoid obscuring other components of optical device shown in FIG. 2B.

Device 100 includes lens assembly 110. In some embodiments, lens assembly 110 includes one or more lenses. In some embodiments, lens assembly 110 is a doublet lens. For example, a doublet lens is selected to reduce spherical aberration and other aberrations (e.g., coma and/or chromatic aberration). In some embodiments, lens assembly 110 is a triplet lens. In some embodiments, lens assembly 110 is a singlet lens. In some embodiments, lens assembly 110 includes two or more separate lenses. In some embodiments, lens assembly 110 includes an aspheric lens. In some embodiments, a working distance of lens assembly 110 is between 10-100 mm (e.g., between 10-90 mm, 10-80 mm, 10-70 mm, 10-60 mm, 10-50 mm, 15-90 mm, 15-80 mm, 15-70 mm, 15-60 mm, 15-50 mm, 20-90 mm, 20-80 mm, 20-70 mm, 20-60 mm, 20-50 mm, 25-90 mm, 25-80 mm, 25-70 mm, 25-60 mm, or 25-50 mm). In some embodiments, when the lens assembly includes two or more lenses, an effective focal length of a first lens (e.g., the lens positioned closest to the pupil plane) is between 10-150 mm (e.g., between 10-140 mm, 10-130 mm, 10-120 mm, 10-110 mm, 10-100 mm, 10-90 mm, 10-80 mm, 10-70 mm, 10-60 mm, 10-50 mm, 15-150 mm, 15-130 mm, 15-120 mm, 15-110 mm, 15-100 mm, 15-90 mm, 15-80 mm, 15-70 mm, 15-60 mm, 15-50 mm, 20-150 mm, 20-130 mm, 20-120 mm, 20-110 mm, 20-100 mm, 20-90 mm, 20-80 mm, 20-70 mm, 20-60 mm, 20-50 mm, 25-150 mm, 25-130 mm, 25-120 mm, 25-110 mm, 25-100 mm, 25-90 mm, 25-80 mm, 25-70 mm, 25-60 mm, 25-50 mm, 30-150 mm, 30-130 mm, 30-120 mm, 30-110 mm, 30-100 mm, 30-90 mm, 30-80 mm, 30-70 mm, 30-60 mm, 30-50 mm, 35-150 mm, 35-130 mm, 35-120 mm, 35-110 mm, 35-100 mm, 35-90 mm, 35-80 mm, 35-70 mm, 35-60 mm, 35-50 mm, 40-150 mm, 40-130 mm, 40-120 mm, 40-110 mm, 40-100 mm, 40-90 mm, 40-80 mm, 40-70 mm, 40-60 mm, 40-50 mm, 45-150 mm, 45-130 mm, 45-120 mm, 45-110 mm, 45-100 mm, 45-90 mm, 45-80 mm, 45-70 mm, 45-60 mm, 45-50 mm, 50-150 mm, 50-130 mm, 50-120 mm, 50-110 mm, 50-100 mm, 50-90 mm, 50-80 mm, 50-70 mm, or 50-60 mm). In some embodiments, for an 8 mm pupil diameter, the lens diameter is 16-24 mm. In some embodiments, for a 7 mm pupil diameter, the lens diameter is 12-20 mm. In some embodiments, the f-number of lens assembly is between 2 and 5. The use of a common lens assembly (e.g., lens assembly 110) in both a wavefront sensor and a contact lens center sensor allows the integration of the wavefront sensor and the contact lens center sensor without needing large diameter optics.

Device 100 also includes a wavefront sensor. In some embodiments, the wavefront sensor includes first light source 120, lens assembly 110, an array of lenses 132 (also called herein lenslets), and first image sensor 140. In some embodiments, the wavefront sensor includes additional components (e.g., one or more lenses 130). In some embodiments, the wavefront sensor does not include such additional components.

Figure 2C:
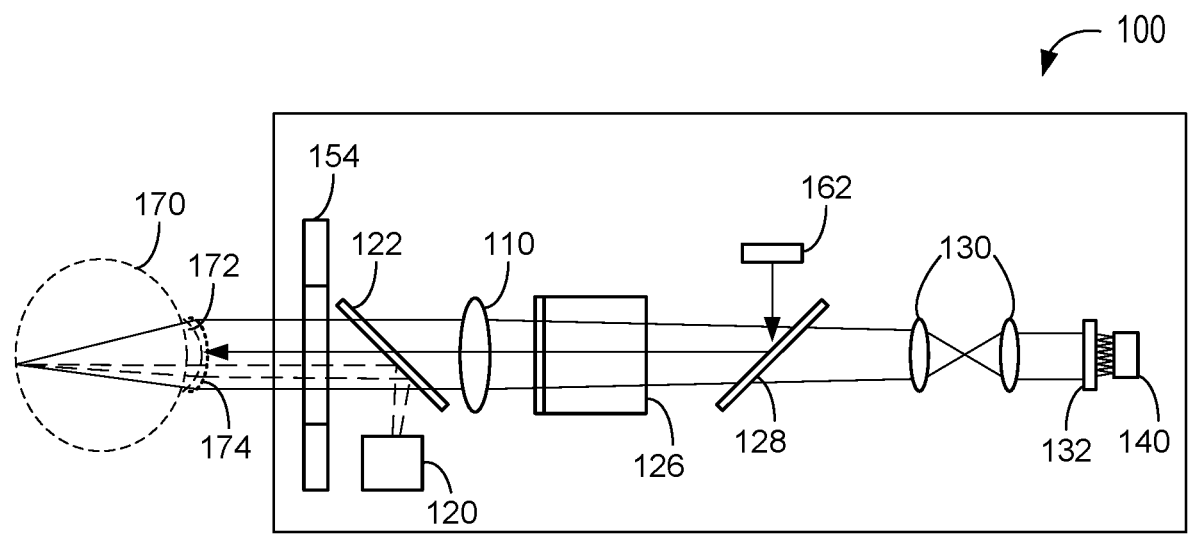
FIG. 2C illustrates wavefront sensing with the optical device shown in FIGS. 2A and 2B, in accordance with some embodiments.

First light source 120 is configured to emit first light and transfer the first light emitted from the first light source toward eye 170, as depicted in FIG. 2C. In some embodiments, device 100 includes FIGS. 2A-2D include eye 170, its components (e.g., cornea 172), and contact lens 174 to illustrate the operations of device 100 with eye 170 and contact lens 174. However, eye 170, its components, and contact lens 174 are not part of device 100.

Turning back to FIG. 2A, in some embodiments, first light source 120 is configured to emit light of a single wavelength or a narrow band of wavelengths. Exemplary first light source 120 includes a laser (e.g., a laser diode) or a light-emitting diode (LED).

In some embodiments, first light source 120 includes one or more lenses to change the divergence of the light emitted from first light source 120 so that the light, after passing through the one or more lenses, is collimated.

In some embodiments, first light source 120 includes a pinhole (e.g., having a diameter of 1 mm or less, such as 400 µm, 500 µm, 600 µm, 700 µm, 800 µm, 900 µm, and 1 mm).

In some cases, an anti-reflection coating is applied on a back surface (and optionally, a front surface) of lens assembly 110 to reduce reflection. In some embodiments, first light source 120 is configured to transfer the first light emitted from first light source 120 off an optical axis of device 100 (e.g., an optical axis of lens assembly 110), as shown in FIG. 2C (e.g., the first light emitted from first light source 120 propagates parallel to, and offset from, the optical axis of lens assembly 110). This reduces back reflection of the first light emitted from first light source 120, by cornea 172, toward first image sensor 140. In some embodiments, the wavefront sensor includes a quarter-wave plate to reduce back reflection of the first light, from lens assembly 110 (e.g., light reflected from lens assembly 110 is attenuated by the quarter-wave plate). In some embodiments, the quarter-wave plate is located between beam steerer 122 and first image sensor 140.

First image sensor 140 is configured to receive light, from eye 170, transmitted through lens assembly 110 and the array of lenses 132. In some embodiments, the light from eye 170 includes light scattered at a retina or fovea of eye 170 (in response to the first light from first light source 120). For example, as shown in FIG. 2C, light from eye 170 passes multiple optical elements, such as beam steerer 122, lens assembly 110, beam steerer 126, beam steerer 128, and lenses 130, and reaches first image sensor 140.

Beam steerer 122 is configured to reflect light from light source 120 and transmit light from eye 170, as shown in FIG. 2C. Alternatively, beam steerer 122 is configured to transmit light from light source 120 and reflect light from eye 170. In some embodiments, beam steerer 122 is a beam splitter (e.g., 50:50 beam splitter, polarizing beam splitter, etc.). In some embodiments, beam steerer 122 is a wedge prism, and when first light source 120 is configured to have a linear polarization, the polarization of the light emitted from first light source 120 is configured to reflect at least partly by the wedge prism. Light of a polarization that is orthogonal to the linear polarization of the light emitted from first light source 120 is transmitted through the wedge prism. In some cases, the wedge prism also reduces light reflected from cornea 172 of eye 170.

In some embodiments, beam steerer 122 is tilted at such an angle (e.g., an angle between the optical axis of device 100 and a surface normal of beam steerer 122 is at an angle less than 45°, such as 30°) so that the space occupied by beam steerer 122 is reduced.

In some embodiments, device 100 includes one or more lenses 130 to modify a working distance of device 100.

The array of lenses 132 is arranged to focus incoming light onto multiple spots, which are imaged by first image sensor 140. As in Shack-Hartmann wavefront sensor, an aberration in a wavefront causes displacements (or disappearances) of the spots on first image sensor 140. In some embodiments, a Hartmann array is used instead of the array of lenses 132. A Hartmann array is a plate with an array of apertures (e.g., through-holes) defined therein.

In some embodiments, one or more lenses 130 and the array of lenses 132 are arranged such that the wavefront sensor is configured to measure a reduced range of optical power. A wavefront sensor that is capable of measuring a wide range of optical power may have less accuracy than a wavefront sensor that is capable of measuring a narrow range of optical power. Thus, when a high accuracy in wavefront sensor measurements is desired, the wavefront sensor can be designed to cover a narrow range of optical power. For example, a wavefront sensor for diagnosing low and medium myopia can be configured with a narrow range of optical power between 0 and −6.0 diopters, with its range centering around −3.0 diopters. Although such a wavefront sensor may not provide accurate measurements for diagnosing hyperopia (or determining a prescription for hyperopia), the wavefront sensor would provide more accurate measurements for diagnosing myopia (or determining a prescription for myopia) than a wavefront sensor that can cover both hyperopia and myopia (e.g., from −6.0 to +6.0 diopters). In addition, there are certain populations in which it is preferable to maintain a center of the range at a non-zero value. For example, in some Asian populations, the optical power may range from +6.0 to −14.0 diopters (with the center of the range at −4.0 diopters), whereas in some Caucasian populations, the optical power may range from +8.0 to −12.0 diopters (with the center of the range at −2.0 diopters). The center of the range can be shifted by moving the lenses (e.g., one or more lens 130 and/or the array of lenses 132). For example, defocusing light from eye 170 can shift the center of the range.

Device 100 further includes a contact lens center sensor (or a corneal vertex sensor). In some embodiments, the contact lens center sensor includes lens assembly 110, second light source 154, and second image sensor 160. In some embodiments, as shown in FIG. 2B, second image sensor 160 is distinct from first image sensor 140. In some embodiments, the wavefront sensor includes additional components that are not included in the contact lens center sensor (e.g., array of lenses 132).

Figure 2D:
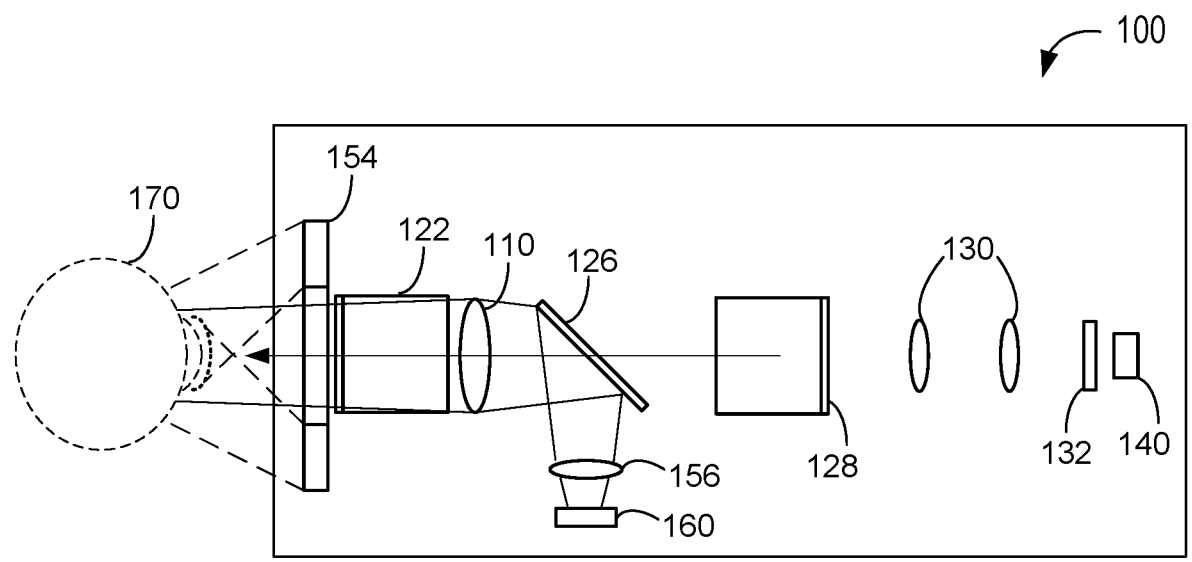
FIG. 2D illustrates imaging with the optical device shown in FIGS. 2A and 2B, in accordance with some embodiments.

Second light source 154 is configured to emit second light and transfer the second light emitted from second light source 154 toward eye 170. As shown in FIG. 2D, in some embodiments, second light source 154 is configured to transfer the second light emitted from second light source 154 toward eye 170 without transmitting the second light emitted from second light source 154 through lens assembly 110 (e.g., second light from second light source 154 is directly transferred to eye 170 without passing through lens assembly 110).

In some embodiments, device 100 includes beam steerer 126 configured to transfer light from eye 170, transmitted through lens assembly 110, toward first image sensor 140 and/or second image sensor 160. For example, when device 100 is configured for wavefront sensing (e.g., when light from first light source 120 is transferred toward eye 170), beam steerer 126 transmits light from eye 170 toward first image sensor 140, and when device 100 is configured for contact lens center determination (e.g., when light from second light source 154 is transferred toward eye 170), beam steerer 126 transmits light from eye 170 toward second image sensor 160.

Second light source 154 is distinct from first light source 120. In some embodiments, first light source 120 and second light source 154 emit light of different wavelengths (e.g., first light source 120 emits light of 900 nm wavelength, and second light source 154 emits light of 800 nm wavelength; alternatively, first light source 120 emits light of 850 nm wavelength, and second light source 154 emits light of 950 nm wavelength).

In some embodiments, beam steerer 126 is a dichroic mirror (e.g., a mirror that is configured to transmit the first light from first light source 120 and reflect the second light from second light source 154, or alternatively, reflect the first light from first light source 120 and transmit the second light from second light source 154). In some embodiments, beam steerer 126 is a movable mirror (e.g., a mirror that can flip or rotate to steer light toward first image sensor 140 and second image sensor 160). In some embodiments, beam steerer 126 is a beam splitter. In some embodiments, beam steerer 126 is configured to transmit light of a first polarization and reflect light of a second polarization that is distinct from (e.g., orthogonal to) the first polarization. In some embodiments, beam steerer 126 is configured to reflect light of the first polarization and transmit light of the second polarization.

In some embodiments, second light source 154 is configured to project a predefined pattern of light on the eye (e.g., patterns shown in FIGS. 4A-4D). In some embodiments, second light source 154 is configured to project an array of spots on the eye. In some embodiments, the array of spots is arranged in a grid pattern (e.g., FIG. 4B).

In some embodiments, second light source 154 includes one or more light emitters (e.g., light-emitting diodes) and diffuser (e.g., a diffuser plate having an array of spots).

Figure 2E:
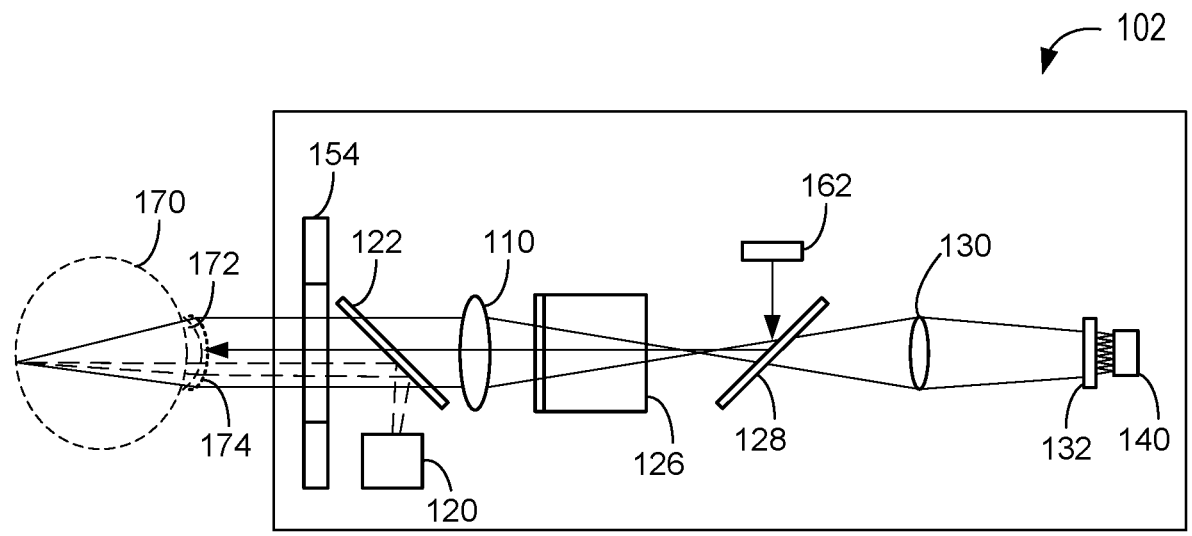
FIGS. 2E and 2F illustrate optical components of an optical device in accordance with some other embodiments.
Figure 2F:
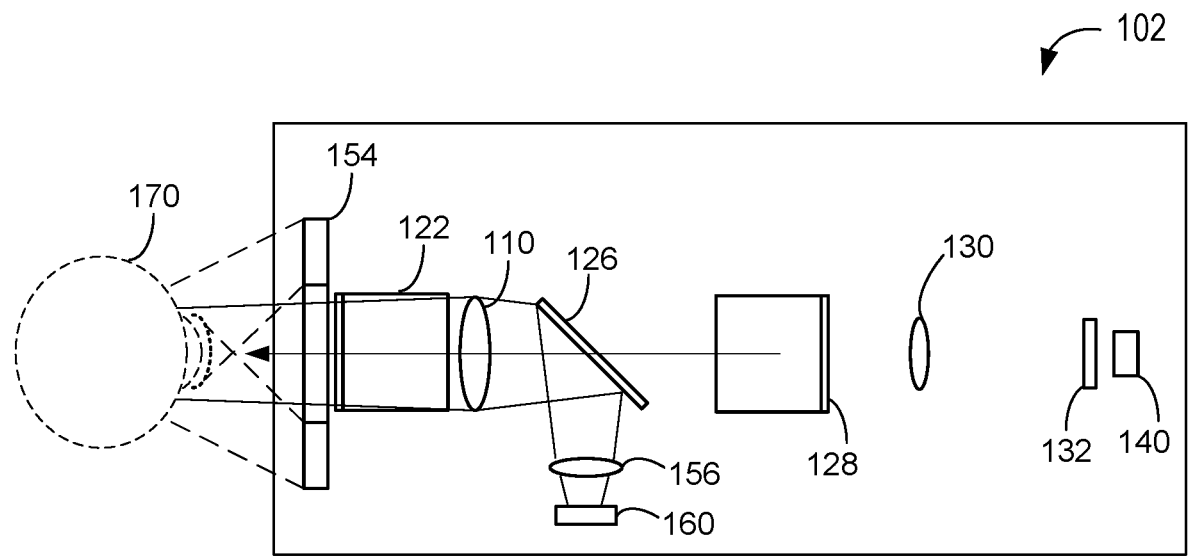

FIGS. 2E and 2F illustrate optical components of optical device 102 in accordance with some other embodiments. Optical device 102 is similar to optical device 100 shown in FIGS. 2A-2D except that optical device 102 includes only one lens 130.

Figure 2G:
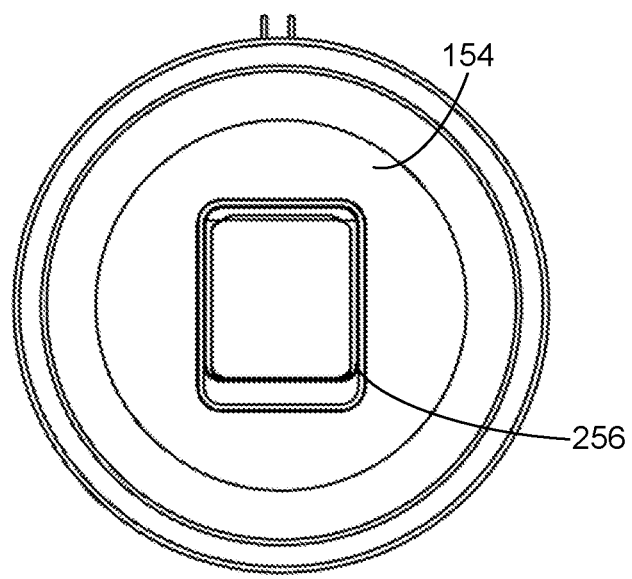
FIG. 2G illustrates a front view of the optical device shown in FIGS. 2A and 2B, in accordance with some embodiments.

FIG. 2G is a front view of optical device 100 in accordance with some embodiments. The side view of optical device 100 shown in FIG. 2G corresponds to a view of optical device 100 seen from a side that is adjacent to second light source 154. In FIG. 2G, optical device 100 includes second light source 154, which has a circular shape with a rectangular hole 256 defined in it. Second light source 154 shown in FIG. 2G projects a pattern of light shown in FIG. 4A.

Turning back to FIG. 2A, second image sensor 160 is configured to receive light, from eye 170. In some embodiments, the light from eye 170 includes light reflected from cornea 172 of eye 170 (in response to the second light from second light source 154). For example, as shown in FIG. 2D, light from eye 170 (e.g., light reflected from cornea 172) interacts with multiple optical elements, such as lens assembly 110, beam steerer 122, lens 124, beam steerer 126, and one or more lenses 156, and reaches second image sensor 160.

The lenses in the contact lens center sensor (e.g., lens assembly 110 and one or more lenses 156) are configured to image a pattern of light projected on cornea 172 onto second image sensor 160. For example, when a predefined pattern of light is projected on cornea 172, the image of the predefined pattern of light detected by second image sensor 160 is used to determine a center of a contact lens on the cornea (or a vertex of the cornea).

Figure 5A:
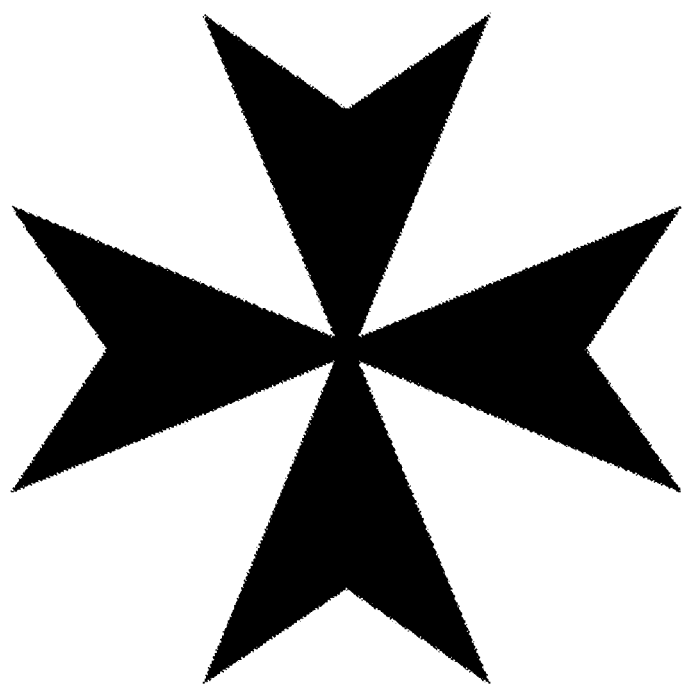
FIGS. 5A and 5B illustrate reference target images in accordance with some embodiments.
Figure 5B:
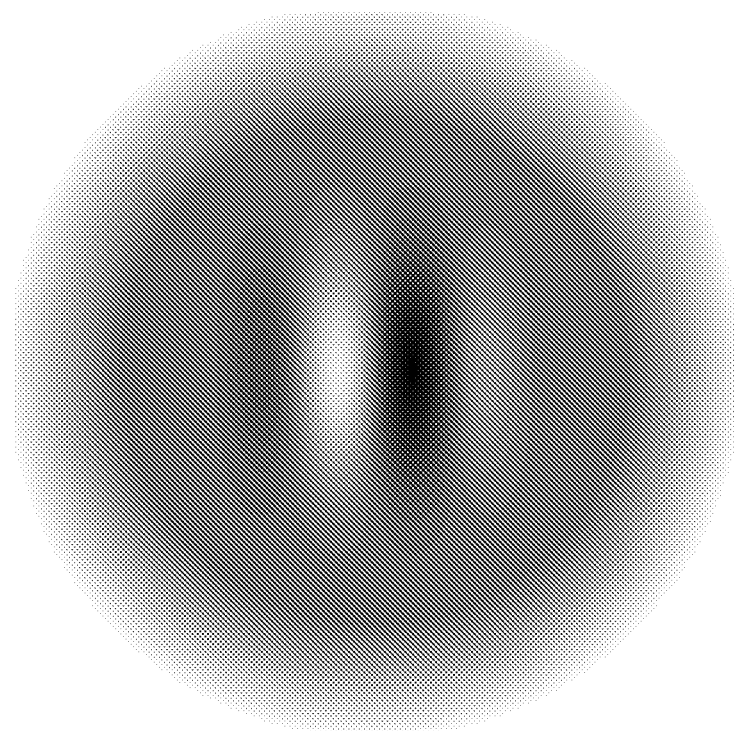

In some embodiments, optical device 100 includes pattern 162 and beam steerer 128. Pattern 162 is an image that is projected toward eye 170 to facilitate positioning of eye 170. In some embodiments, pattern 162 includes an image of an object (e.g., balloon), an abstract shape (e.g., a cross as shown in FIG. 5A), or a pattern of light (e.g., a shape having a blurry edge as shown in FIG. 5B).

In some embodiments, beam steerer 128 is a dichroic mirror (e.g., a mirror that is configured to transmit the light from eye 170 and reflect light from pattern 162, or alternatively, reflect light from eye 170 and transmit light from pattern 162). In some embodiments, beam steerer 128 is a movable mirror. In some embodiments, beam steerer 128 is a beam splitter. In some embodiments, beam steerer 128 is configured to transmit light of a first polarization and reflect light of a second polarization that is distinct from (e.g., orthogonal to) the first polarization. In some embodiments, beam steerer 128 is configured to reflect light of the first polarization and transmit light of the second polarization.

FIG. 2C illustrates operation of device 100 for wavefront sensing without operations for determining a contact lens center and FIG. 2D illustrates operation of device 100 for determining a contact lens center without wavefront sensing. In some embodiments, device 100 sequentially operates between wavefront sensing and determining a contact lens center. For example, in some cases, device 100 performs wavefront sensing and subsequently, determines a contact lens center. In some other cases, device 100 determines a contact lens center, and subsequently performs wavefront sensing. In some embodiments, device 100 switches between wavefront sensing and determining a contact lens center. In some embodiments, device 100 repeats wavefront sensing and determining a contact lens center. In some embodiments, device 100 operates for wavefront sensing concurrently with determining a contact lens center (e.g., light from first light source 120 and light from second light source 154 are delivered toward eye 170 at the same time, and first image sensor 140 and second image sensor 160 collect images at the same time). For brevity, such details are not repeated herein.

In some embodiments, light from pattern 162 is projected toward eye 170 while device 100 operates for wavefront sensing (as shown in FIG. 2C). In some embodiments, light from pattern 162 is projected toward eye 170 while device 100 operates for determining a contact lens center (as shown in FIG. 2D).

Figure 3:
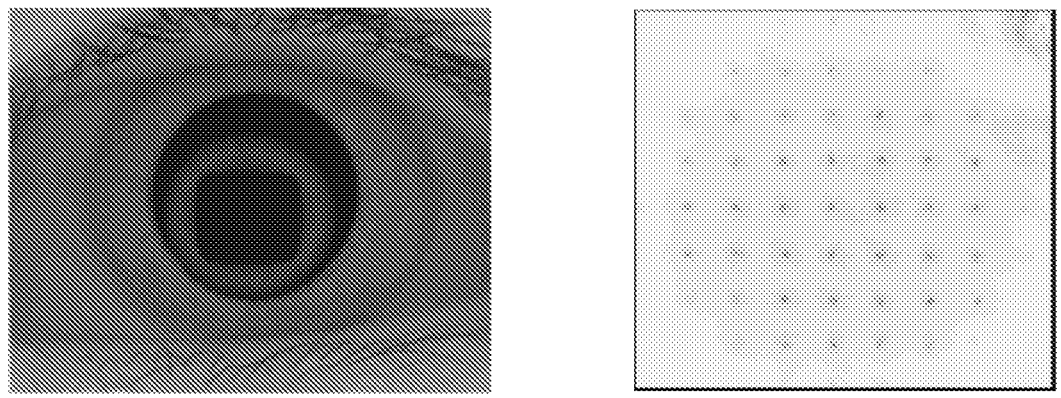
FIG. 3 illustrates an image of an eye and an image from wavefront sensing in accordance with some embodiments.

FIG. 3 illustrates an image of an eye (collected by second image sensor 160) and an image from wavefront sensing (collected by first image sensor 140) in accordance with some embodiments. In some embodiments, device 100 collects the image of the eye and the image from wavefront sensing concurrently. In some embodiments, device 100 stores the image of the eye and the image from wavefront sensing concurrently.

FIGS. 4A and 4B illustrates example illumination patterns, their projection on eyes, and determination of contact lens vertices in accordance with some embodiments.

FIG. 4A shows, on the left side, an example pattern of light (colored black). The pattern of light shown in FIG. 4A is a contiguous pattern that includes a circular shape with a hollow rectangular region inside the circular shape (e.g., in the middle of the circular shape).

FIG. 4A shows, in the middle, projection of the pattern of light on an eye. Similar to the images shown in FIG. 1E, a boundary of a pupil can be determined from an image of the projection of the pattern of light on an eye.

In addition, a center of the projected pattern is determined (e.g., a center of the dark rectangular region shown on the right side of FIG. 4A). The center of the projected pattern corresponds to a corneal vertex. The corneal vertex is adjacent to a center of a contact lens located on the cornea, and in some cases, the corneal vertex is used as a proxy (or an estimate) of the center of the contact lens.

FIG. 4B shows, on the left side, another example pattern of light. The pattern of light shown in FIG. 4B has a grid pattern that is arranged in a circular shape with a hollow circular region inside.

FIG. 4B shows, in the middle, projection of the pattern of light on an eye.

The right side of FIG. 4B shows that a center of the projected pattern is determined.

FIG. 4C shows, on the left side, example light source 154 in accordance with some embodiments. Light source 154 shown in FIG. 4C includes a plurality of light emitting elements 164 (e.g., light emitting diodes) for projecting a predefined pattern of light. For example, in FIG. 4C, two light emitting elements 164 are located above the hole 256 and two light emitting elements 164 are located below the hole 256. This allows projection of a pattern of light shown in the middle of FIG. 4C, which includes a plurality of spots 402 (e.g., four spots 402).

FIG. 4C shows, on the right side, projection of the pattern of light on an eye and a center of the projected pattern, which corresponds to a visual axis of the eye.

Although FIG. 4C shows a predefined pattern of light including four spots, in some embodiments, more or fewer spots may be used. For example, a predefined pattern of light including five, six, seven, eight, nine, or more spots or a predefined pattern of light including three or two spots may be used. In some embodiments, the plurality of spots (or a plurality of light emitting elements corresponding to the plurality of spots) is arranged in such a way that a geometric center of the plurality of spots corresponds to a visual axis of the eye.

FIG. 4D illustrates, on the left side, example light source 154 in accordance with some embodiments. Light source 154 shown in FIG. 4D includes a plurality of light emitting elements 164 (e.g., light emitting diodes) for projecting a grid pattern (similar to the pattern of light shown in FIG. 4B). FIG. 4D shows, on the right side, projection of the grid pattern of light emitted by the light source 154 shown on the left side of FIG. 4D.

As used herein, a pattern of light refers to shape(s) and/or distribution of one or more illumination areas. For example, the pattern of light may include a single contiguous illumination area having a particular shape (e.g., a rectangle, a circle, or a donut, as shown in FIG. 4A). Alternatively, the pattern of light may include a particular arrangement of multiple separate spots as shown in FIGS. 4B and 4C.

Figure 6:
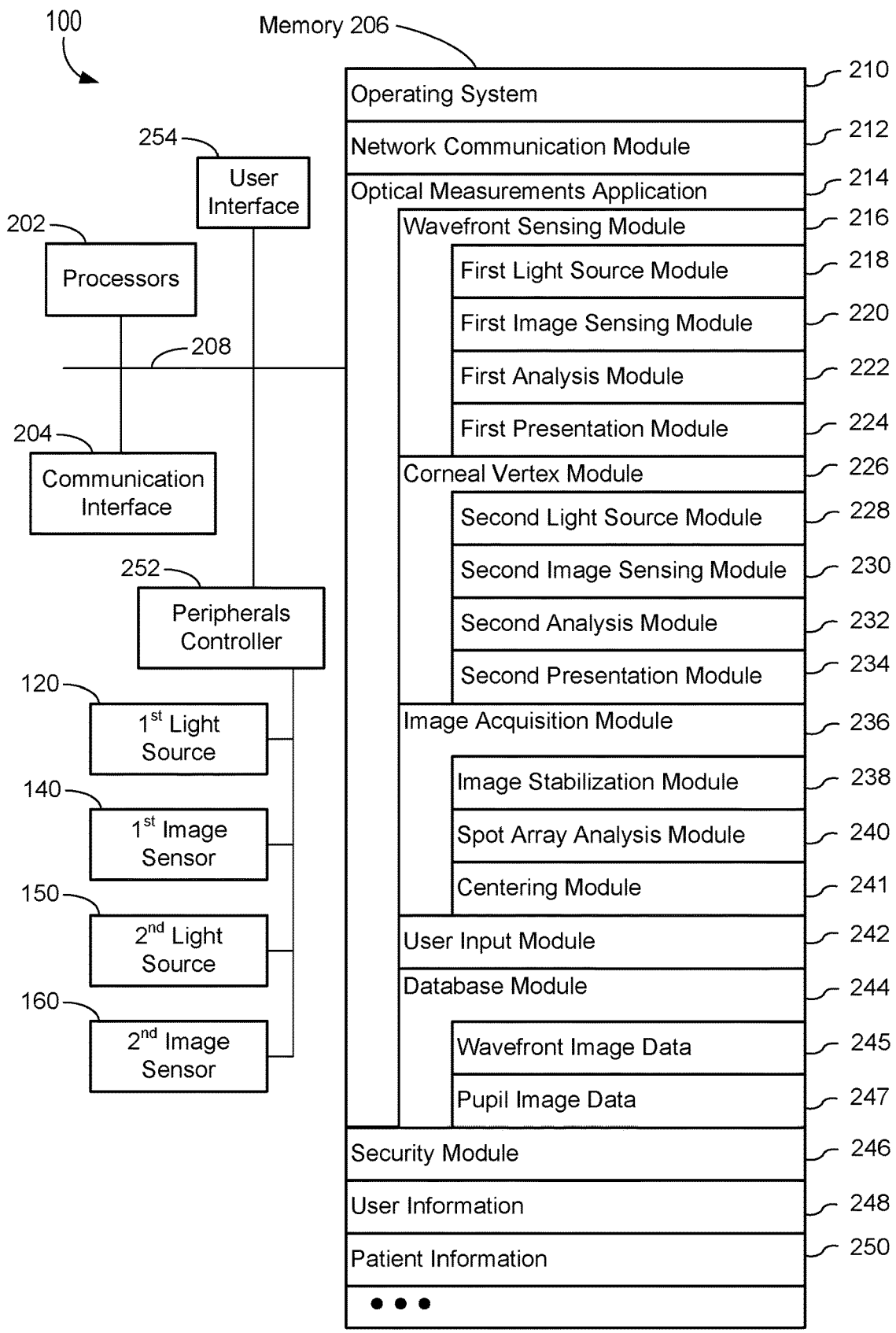
FIG. 6 is a block diagram illustrating electronic components of an optical device in accordance with some embodiments.

FIG. 6 is a block diagram illustrating electronic components of device 100 in accordance with some embodiments.

Device 100 typically includes one or more processing units 202 (central processing units, application processing units, application-specific integrated circuit, etc., which are also called herein processors), one or more network or other communications interfaces 204, memory 206, and one or more communication buses 208 for interconnecting these components. In some embodiments, communication buses 208 include circuitry (sometimes called a chipset) that interconnects and controls communications between system components. In some embodiments, device 100 includes a user interface 254 (e.g., a user interface having a display device, which can be used for displaying acquired images, one or more buttons, and/or other input devices). In some embodiments, device 100 also includes peripherals controller 252, which is configured to control operations of other electrical components of device 100, such as first light source 120, first image sensor 140, second light source 150, and second image sensor 160 (e.g., initiating respective light sources to emit light, and/or receiving information, such as images, from respective image sensors).

In some embodiments, communications interfaces 204 include wired communications interfaces and/or wireless communications interfaces (e.g., Wi-Fi, Bluetooth, etc.).

Memory 206 of device 100 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 206 may optionally include one or more storage devices remotely located from the processors 202. Memory 206, or alternately the non-volatile memory device(s) within memory 206, comprises a computer readable storage medium (which includes a non-transitory computer readable storage medium and/or a transitory computer readable storage medium). In some embodiments, memory 206 includes a removable storage device (e.g., Secure Digital memory card, Universal Serial Bus memory device, etc.). In some embodiments, memory 206 or the computer readable storage medium of memory 206 stores the following programs, modules and data structures, or a subset thereof:

- operating system 210 that includes procedures for handling various basic system services and for performing hardware dependent tasks;
- network communication module (or instructions) 212 that is used for connecting device 100 to other computers (e.g., clients and/or servers) via one or more communications interfaces 204 and one or more communications networks, such as the Internet, other wide area networks, local area networks, metropolitan area networks, and so on;
- optical measurements application 214 that controls operations of the light sources and the image sensors; and
- security module 246 that protects data stored on device 100 during its storage on device 100 and/or transmission to and from another computer (e.g., clients and/or servers); for example, security module 246 may include an encryption module for encrypting data stored on device 100, a decryption module for decrypting encrypted data, either stored on device 100 or received from another computer, and an authentication module for authenticating a user of device 100 and/or a remote computer for communication with device 100 (e.g., for sending and/or receiving data).

In some embodiments, memory 206 also includes one or both of:

- user information 248 (e.g., information necessary for authenticating a user of device 100); and
- patient information 250 (e.g., optical measurement results and/or information that can identify patients whose optical measurement results are stored on device 100).

In some embodiments, optical measurements application 214 includes the following programs, modules and data structures, or a subset or superset thereof:

- wavefront sensing module 216 configured for operating the wavefront sensor in device 100;
- corneal vertex module 226 configured for operating the contact lens center sensor in device 100;
- image acquisition module 236 configured for analyzing images collected by respective image sensors of device 100;
- user input module 242 configured for handling user inputs on device 100 (e.g., pressing of buttons of device 100, etc.); and
- database module 244 configured to assist storage of data on device 100 and retrieval of data from device 100 (in some embodiments, database module 244 operates in conjunction with security module 246).

In some embodiments, database module 244 includes the following programs and modules, or a subset or superset thereof:

- wavefront image data 245 including information representing the light received by the first image sensor (e.g., images received by the first image sensor); and
- pupil image data 247 including information representing the light received by the second image sensor (e.g., images received by the second image sensor).

In some embodiments, wavefront sensing module 216 includes the following programs and modules, or a subset or superset thereof:

- first light source module 218 configured for initiating first light source 120 (through peripherals controller 252) to emit light;
- first image sensing module 220 configured for receiving images from first image sensor 140;
- first analysis module 222 configured for analyzing images received from first image sensor 140; and
- first presentation module 224 configured for presenting measurement and analysis results from first analysis module 222 (e.g., graphically displaying images received from first image sensor 140, presenting aberrations shown in images received from first image sensor 140, sending the results to another computer, etc.).

In some embodiments, corneal vertex module 226 includes the following programs and modules, or a subset or superset thereof:

- second light source module 228 configured for initiating second light source 154 (through peripherals controller 252) to emit light;
- second image sensing module 230 configured for receiving images from second image sensor 160;
- second analysis module 232 configured for analyzing images received from second image sensor 160 (e.g., determining a center of a projected pattern of light); and
- second presentation module 234 configured for presenting measurement and analysis results from second analysis module 232 (e.g., graphically displaying images received from second image sensor 160, presenting cornea curvatures determined from images received from second image sensor 160, sending the results to another computer, etc.).

In some embodiments, image acquisition module 236 includes the following programs and modules, or a subset or superset thereof:

image stabilization module 238 configured for reducing blurring during acquisition of images by image sensors;

spot array analysis module 240 configured for analyzing spot arrays (e.g., measuring displacements and/or disappearances of spots in the spot arrays); and/or centering module 241 configured for determining a center of a projected pattern of light.

In some embodiments, first image sensing module 220 initiates execution of image stabilization module 238 to reduce blurring during acquisition of images by first image sensor 140, and second image sensing module 230 initiates execution of image stabilization module 238 to reduce blurring during acquisition of images by second image sensor 160.

In some embodiments, first analysis module 222 initiates execution of spot array analysis module 240 to analyze spot arrays in images acquired by first image sensor 140, and second analysis module 232 initiates execution of spot array analysis module 240 to analyze spot arrays in images acquired by second image sensor 160.

In some embodiments, first analysis module 222 initiates execution of spot array analysis module 240 to analyze spot arrays in images acquired by first image sensor 140, and second analysis module 232 initiates execution of centering module 241 to analyze images acquired by second image sensor 160.

Each of the above identified modules and applications correspond to a set of instructions for performing one or more functions described above. These modules (i.e., sets of instructions) need not be implemented as separate software programs, procedures or modules, and thus various subsets of these modules may be combined or otherwise re-arranged in various embodiments. In some embodiments, memory 206 may store a subset of the modules and data structures identified above. Furthermore, memory 206 may store additional modules and data structures not described above.

Notwithstanding the discrete blocks in FIG. 6, these figures are intended to be a functional description of some embodiments, although, in some embodiments, the discrete blocks in FIG. 6 can be a structural description of functional elements in the embodiments. One of ordinary skill in the art will recognize that an actual implementation might have the functional elements grouped or split among various components. In practice, and as recognized by those of ordinary skill in the art, items shown separately could be combined and some items could be separated. For example, in some embodiments, security module 246 is part of optical measurements application 214. In other embodiments, wavefront sensing module 216 and corneal vertex module 226 are implemented as separate applications.

FIG. 7 is a flowchart representing method 700 for optical measurements (e.g., wavefront sensing and locating a contact lens center or a corneal vertex) with an optical device, in accordance with some embodiments.

In some embodiments, method 700 includes (702) determining one or more aberrations of a combination of an eye and a contact lens (e.g., a scleral lens; a soft contact lens; and a hard contact lens, including a hard corneal lens, such as a rigid gas permeable lens and an orthokeratology lens; etc.) positioned adjacent to the eye and determining a location of a center of the contact lens by using a single optical device (e.g., device 100 shown in FIGS. 2A and 2B).

The single optical device includes a lens assembly (e.g., lens assembly 110).

The single optical device also includes a wavefront sensor. The wavefront sensor includes a first light source (e.g., light source 120) configured to emit first light and transfer the first light emitted from the first light source toward the combination of the eye and the contact lens (e.g., by means of beam steerer 122). The wavefront sensor also includes the lens assembly for collecting light from the combination of the eye and the contact lens. The wavefront sensor further includes: an array of lenses (e.g., array of lenses 132) that is distinct from the lens assembly, the array of lenses configured to focus light transmitted through the lens assembly; and a first image sensor (e.g., first image sensor 140) configured to receive light, from the combination of the eye and the contact lens, transmitted through the lens assembly and the array of lenses.

The single optical device further includes a contact lens center sensor (also called a corneal vertex sensor). The contact lens center sensor includes a second light source (e.g., light source 154) configured to emit second light and transfer the second light emitted from the second light source toward the combination of the eye and the contact lens. The contact lens center sensor also includes the lens assembly for collecting light from the combination of the eye and the contact lens. The contact lens center sensor further includes one or more lenses (e.g., one or more lenses 156) configured to focus light transmitted through the lens assembly, the one or more lenses being distinct and separate from the array of lenses; and a second image sensor (e.g., second image sensor 160) configured to receive light, from the combination of the eye and the contact lens, transmitted through the lens assembly and the one or more lenses.

In some embodiments, the method includes (704) determining the one or more aberrations of the combination of the eye and the contact lens based on information corresponding to the light received by the first image sensor (e.g., from wavefront sensing); and determining the location of the vertex of the cornea or the contact lens based on information corresponding to the light received by the second image sensor (e.g., a center of the projected pattern of light).

In some embodiments, the method includes (706) concurrently transferring the first light emitted from the first light source toward the combination of the eye (e.g., FIG. 2C) and the contact lens while transferring the second light emitted from the second light source toward the combination of the eye and the contact lens (e.g., FIG. 2D).

In some embodiments, the method includes (708) projecting an image of a reference toward the eye concurrently with transferring the first light emitted from the first light source toward the combination of the eye and the contact lens and transferring the second light emitted from the second light source toward the combination of the eye and the contact lens (e.g., an image of pattern 162 is projected toward eye 170 as shown in FIGS. 2C and 2D).

In some embodiments, the method includes (710) concurrently receiving light with the first image sensor while receiving light with the second image sensor.

In some embodiments, the method includes (712) sequentially transferring the first light emitted from the first light source toward the combination of the eye and the contact lens and transferring the second light emitted from the second light source toward the combination of the eye and the contact lens (e.g., transferring the second light toward the combination of the eye and the contact lens subsequent to transferring the first light toward the combination of the eye and the contact lens, or transferring the first light toward the combination of the eye and the contact lens subsequent to transferring the second light toward the combination of the eye and the contact lens).

In some embodiments, the method includes (714) sequentially receiving light with the first image sensor and receiving light with the second image sensor.

In some embodiments, the first light has a first pattern (e.g., a single spot from projecting a narrow laser beam on the combination of the eye and the contact lens) when projected on the combination of the eye and the contact lens; and the second light has a second pattern when projected on the combination of the eye and the contact lens (e.g., a shape of a donut or a coin as shown in FIG. 4A). In some embodiments, the first pattern is distinct from the second pattern. In some embodiments, the first pattern includes a first array of spots; and/or the second pattern includes a second array of spots. In some embodiments, the first pattern is identical to the second pattern.

In some embodiments, the location of the center of the contact lens is determined based on information representing to the light received by the second image sensor (e.g., an image of the projected pattern of light).

In some embodiments, the method includes (716) storing information representing the light received by the first image sensor; and storing information representing the light received by the second image sensor in conjunction with the information representing the light received by the first image sensor (e.g., both wavefront image data 245 and pupil image data 247 stored in memory 206).

In some embodiments, the method includes (718) storing information representing the light received by the first image sensor; and storing information representing the location of the center of the contact lens in conjunction with the information representing the light received by the first image sensor. For example, the location of the center of the contact lens relative to the center of the pupil is stored (e.g., as angles θ and φ) instead of storing the entire image received by the second image sensor.

It should be understood that the particular order in which the operations in FIG. 7 have been described is merely exemplary and is not intended to indicate that the described order is the only order in which the operations could be performed. One of ordinary skill in the art would recognize various ways to reorder the operations described herein. For example, storing information representing the light received by the first image sensor may be performed before storing information representing the light received by the second image sensor. In another example, storing information representing the light received by the second image sensor may be performed before storing information representing the light received by the first image sensor. In yet another example, storing information representing the light received by the first image sensor is performed concurrently with storing information representing the light received by the second image sensor (e.g., storing information representing the light received by the first image sensor at least partially overlaps in time with storing information representing the light received by the second image sensor). Additionally, it should be noted that details of other processes described herein with respect to method 800, method 900, method 1000, and method 1100 are also applicable in an analogous manner to method 700 described herein with respect to FIG. 7. For brevity, these details are not repeated here.

Figure 8:
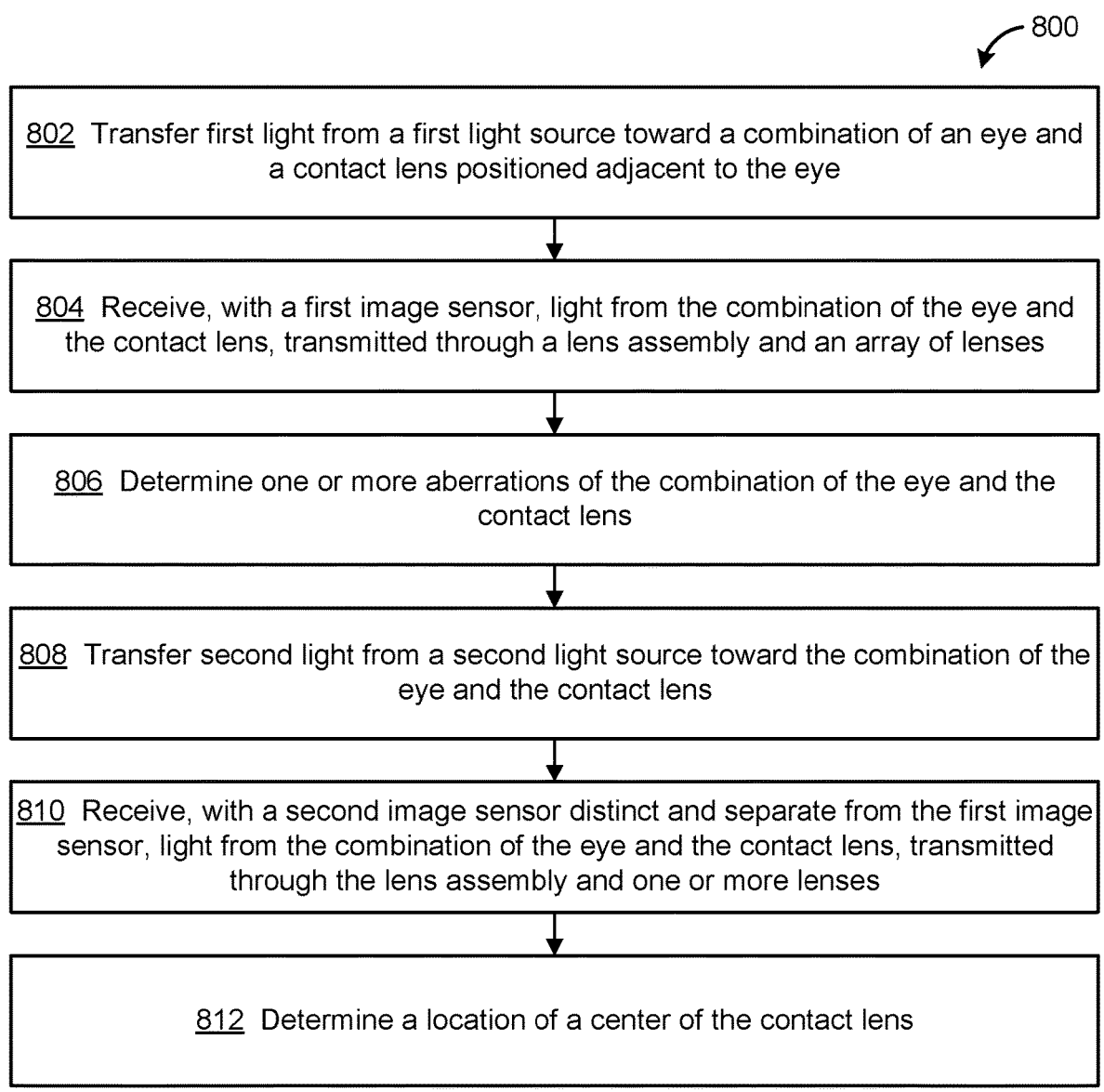
FIG. 8 is a flowchart representing a method of optical measurements with an optical device, in accordance with some embodiments.

FIG. 8 is a flowchart representing method 800 of optical measurements (e.g., wavefront sensing and determining a center of a contact lens or a vertex of a cornea) with an optical device (e.g., device 100), in accordance with some embodiments.

Method 800 includes (802) transferring first light from a first light source toward a combination of an eye and a contact lens positioned adjacent to the eye (e.g., transferring light from first light source 120 as shown in FIG. 2C).

Method 800 includes (804) receiving, with a first image sensor, light from the combination of the eye and the contact lens, transmitted through a lens assembly and an array of lenses (e.g., light from the combination of the eye and the contact lens is received by first image sensor 140 as shown in FIG. 2C).

Method 800 includes (806) determining one or more aberrations of the combination of the eye and the contact lens (e.g., from the pattern, shown on the right side of FIG. 3, one or more aberrations of the combination of the eye and the contact lens are determined).

Method 800 includes (808) transferring second light from a second light source toward the combination of the eye and the contact lens (e.g., transferring light from second light source 154 as shown in FIG. 2D).

Method 800 includes (810) receiving, with a second image sensor distinct and separate from the first image sensor, light from the combination of the eye and the contact lens, transmitted through the lens assembly and one or more lenses (e.g., light from the combination of the eye and the contact lens is received by second image sensor 160 as shown in FIG. 2D).

Method 800 includes (812) determining a location of a center of the contact lens (e.g., the location of the center of the contact lens is determined from, or estimated to be, a center of the projected pattern of light).

It should be understood that the particular order in which the operations in FIG. 8 have been described is merely exemplary and is not intended to indicate that the described order is the only order in which the operations could be performed. One of ordinary skill in the art would recognize various ways to reorder the operations described herein. For example, the first light could be transferred toward the combination of the eye and the contact lens before transferring the second light toward the combination of the eye and the contact lens, or alternatively, the second light could be transferred toward the combination of the eye and the contact lens before transferring the first light toward the combination of the eye and the contact lens. Additionally, it should be noted that details of other processes described herein with respect to method 700, method 900, method 1000, and method 1100 are also applicable in an analogous manner to method 800 described above with respect to FIG. 8. For example, the transferring, receiving, and determining operations, described above with reference to method 800 optionally have one or more of the characteristics of the transferring, receiving, and determining operations described herein with reference to method 700 described herein. For brevity, these details are not repeated here.

Figure 9:
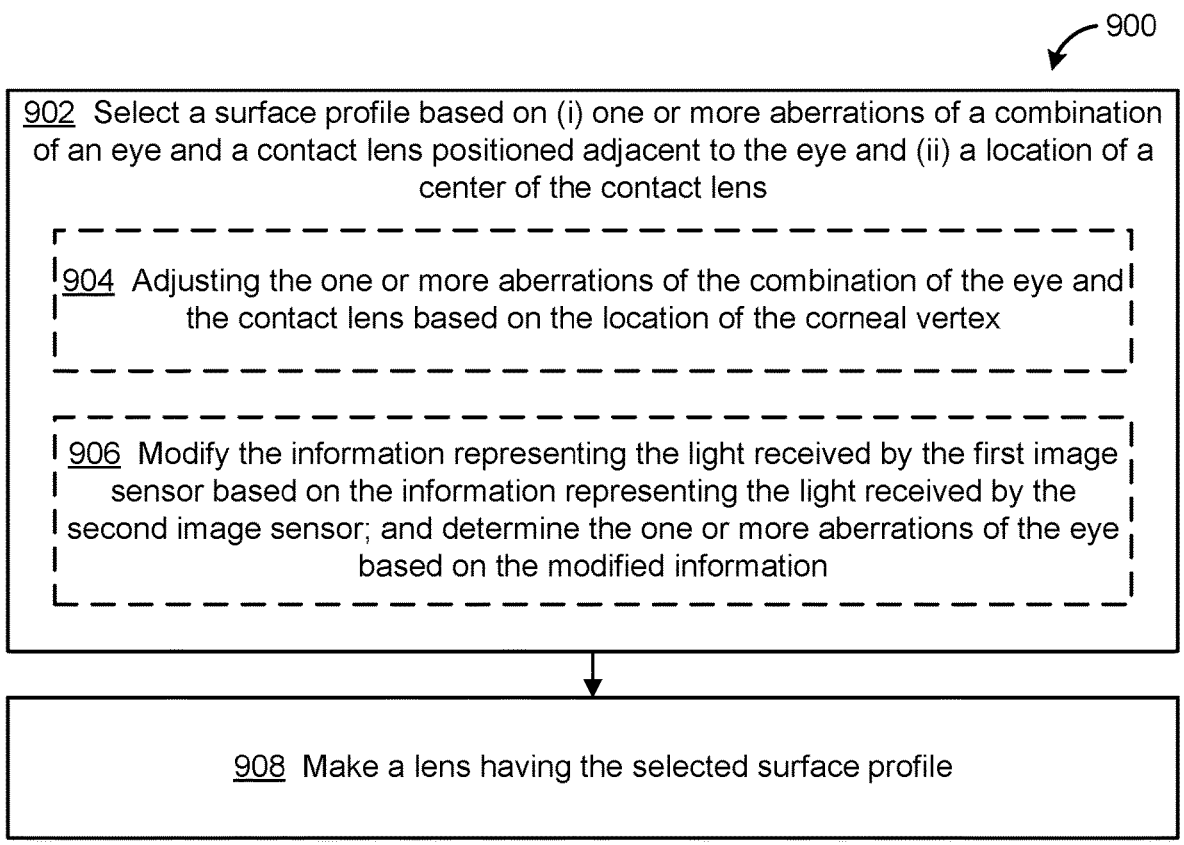
FIG. 9 is a flow chart representing a method of making a corrective lens in accordance with some embodiments.

FIG. 9 is a flow chart representing method 900 of making a corrective lens (e.g., a contact lens) in accordance with some embodiments.

Method 900 includes (902) selecting a surface profile (e.g., offset-corrected modified surface profile $S_{OCM}(\theta, \varphi)$) based on (i) one or more aberrations of a combination of an eye and a contact lens positioned adjacent to the eye and (ii) a location of a center of the contact lens.

In some embodiments, the method includes (904) adjusting the one or more aberrations of the combination of the eye and the contact lens based on the location of the corneal vertex (e.g., adjusting changes-in-a-surface-profile $S_C(\theta, \varphi)$ based on angles θ and φ).

In some embodiments, the method includes (906) modifying the information representing the light received by the first image sensor based on the information representing the light received by the second image sensor; and determining the one or more aberrations of the eye based on the modified information. For example, device 100, instead of utilizing the wavefront sensing results directly, shifts the results of wavefront sensing based on the offset of the center of pupil from the center of the contact lens, and determines the one or more aberrations of the eye based on the shifted results of wavefront sensing.

The method also includes (908) making a lens having the selected surface profile. For example, the lens is cut from a lens material (e.g., polymethyl methacrylate, silicone acrylate, fluorocarbon acrylate, fluorocarbon sulfone, hexafocon, enfulfocon, oprifocon, itafluorofocon, etc.) to have the selected surface profile. In some cases, the lens is machined (e.g., using a computer numerical control machine). In some cases, the lens is made by three-dimensional printing to have the selected surface profile.

Although FIG. 9 illustrates method 900 involving selecting a surface profile based on (i) one or more aberrations of a combination of an eye and a contact lens positioned adjacent to the eye and (ii) a location of a center of the contact lens, in some cases, a lens is made without selecting the surface profile based in part on the location of the center of the contact lens. Additionally, it should be noted that details of other processes described herein with respect to method 700, method 800, method 1000, and method 1100 are also applicable in an analogous manner to method 900 described herein with respect to FIG. 9. For brevity, these details are not repeated here.

Figure 10:
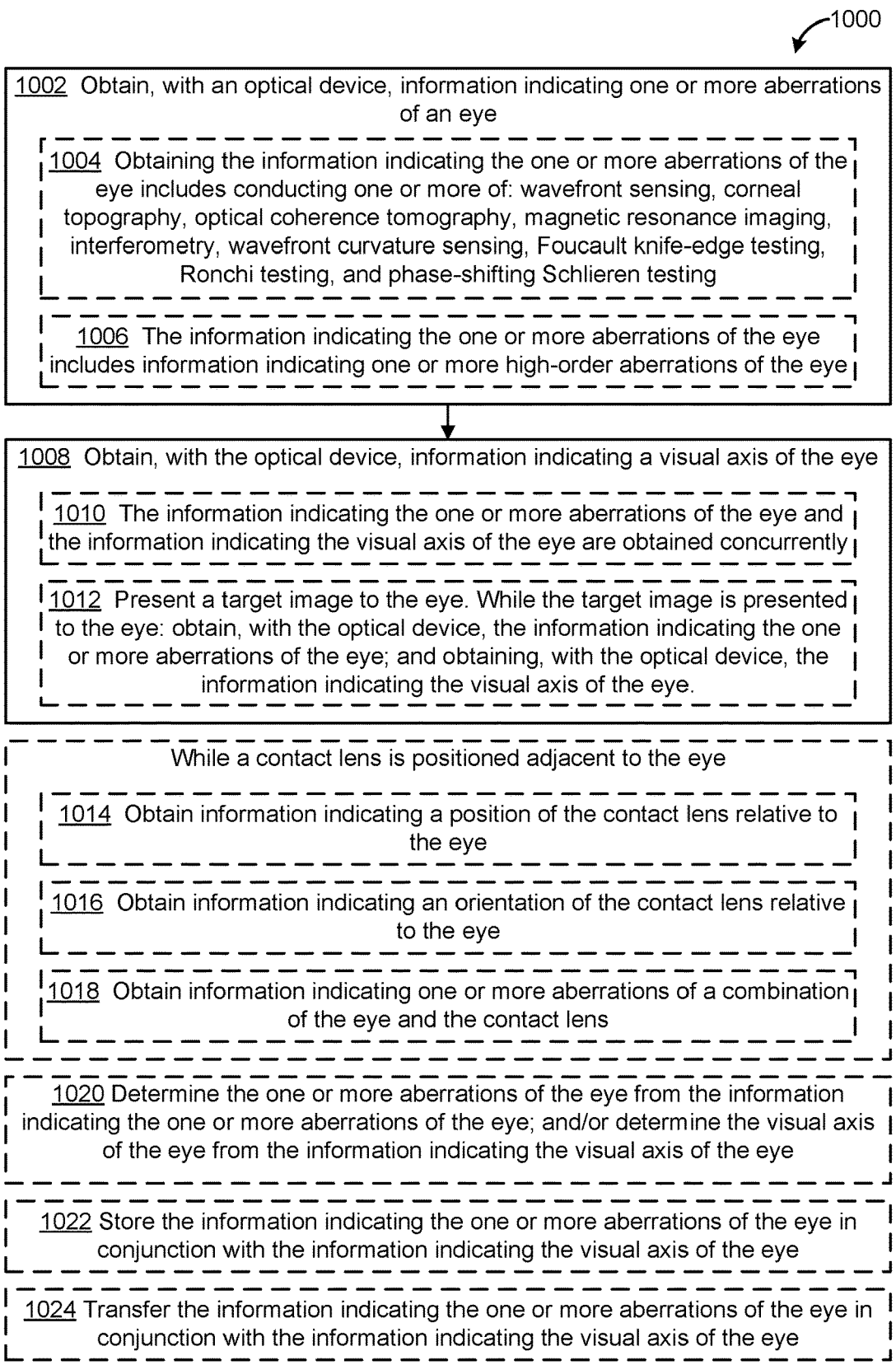
FIG. 10 is a flowchart representing a method of optical measurements with an optical device, in accordance with some embodiments.

FIG. 10 is a flowchart representing method 1000 of optical measurements with an optical device, in accordance with some embodiments.

Method 1000 includes (1002) obtaining, with an optical device, information indicating one or more aberrations of an eye.

In some embodiments, obtaining the information indicating the one or more aberrations of the eye includes (1004) conducting one or more of: wavefront sensing, corneal topography, optical coherence tomography, magnetic resonance imaging, interferometry, wavefront curvature sensing, Foucault knife-edge testing, Ronchi testing, and phase-shifting Schlieren testing. For example, the wavefront sensor in the optical device 100 illustrated in FIGS. 2A-2D may be used for wavefront sensing operation.

In some embodiments, the information indicating the one or more aberrations of the eye includes (1006) information indicating one or more high-order aberrations of the eye (e.g., aberrations higher than astigmatism in the Zernike polynomial model of aberrations, such as trefoil, coma, quadrafoil, spherical aberration, and secondary astigmatism). In comparison, low-order aberrations typically include defocus (which results in nearsightedness or farsightedness) and astigmatism.

Method 1000 also includes (1008) obtaining, with the optical device, information indicating a visual axis of the eye. In some embodiments, obtaining the information indicating a visual axis of the eye includes illuminating the eye with a predefined pattern of light and collecting an image of the eye while the eye is illuminated with the predefined pattern of light (e.g., FIGS. 1F-1G and FIGS. 4A-4C).

In some embodiments, the information indicating the one or more aberrations of the eye and the information indicating the one or more of the visual axis of the eye, the center of the pupil of the eye, and the corneal vertex are obtained (1010) concurrently. For example, light having a first wavelength (e.g., a visible light) and light having a second wavelength (e.g., an infrared light) are projected concurrently toward the eye where the light having the first wavelength is used for determining one or more aberrations of the eye and the light having the second wavelength is used for determining the visual axis of the eye.

In some embodiments, method 1000 includes (1012) presenting a target image (e.g., light provided from a wavefront sensor for wavefront sensing or an image provided in addition to, or instead of, the light provided from the wavefront sensor, such as FIGS. 5A-5B) to the eye; and, while the target image is presented to the eye: obtaining, with the optical device, the information indicating the one or more aberrations of the eye; and obtaining, with the optical device, the information indicating the one or more of the visual axis of the eye, the center of the pupil of the eye, and the corneal vertex. Because the information indicating the one or more aberrations of the eye and the information indicating the one or more of the visual axis of the eye, the center of the pupil of the eye, and the corneal vertex are obtained while the eye is gazing at the target image, the visual axis of the eye and the one or more aberrations of the eye correspond to each other.

In some embodiments, method 1000 includes, while a contact lens is positioned adjacent to the eye, (1014) obtaining information indicating a position of the contact lens relative to the eye (e.g., an image of the contact lens positioned on the eye, which indicates the position of the contact lens on the eye, is obtained). In some embodiments, the information indicating the position of the contact lens relative to the eye is obtained with the optical device.

In some embodiments, method 1000 includes, while the contact lens is positioned adjacent to the eye, (1016) obtaining information indicating an orientation of the contact lens relative to the eye (e.g., an image of the contact lens positioned on the eye, which indicate the orientation of the contact lens on the eye, is obtained). In some embodiments, the information indicating the orientation of the contact lens relative to the eye is obtained with the optical device.

In some embodiments, method 1000 includes, while the contact lens is positioned adjacent to the eye, (1018) obtaining information indicating one or more aberrations of a combination of the eye and the contact lens. In some embodiments, the information indicating the one or more aberrations of the combination of the eye and the contact lens is obtained with the optical device.

In some embodiments, method 1000 includes (1020) at least one of: determining the one or more aberrations of the eye from the information indicating the one or more aberrations of the eye (e.g., the one or more aberrations of the eye are determined from the image collected by the first image sensor 140 shown in FIG. 2C; determining the visual axis of the eye from the information indicating the visual axis of the eye (e.g., the visual axis of the eye is determined from the image collected by the second image sensor 160 shown in FIG. 2D); determining the center of the pupil of the eye from the information indicating the center of the pupil of the eye; and determining the corneal vertex of the eye from the information indicating the corneal vertex of the eye. In some embodiments, the information indicating the one or more of the visual axis of the eye, the information indicating the center of the pupil of the eye, and the information indicating the corneal vertex are identical (e.g., an image of the eye collected while a predefined pattern of light illuminates the eye).

In some embodiments, method 1000 includes (1022) storing the information indicating the one or more aberrations of the eye in conjunction with the information indicating the one or more of the visual axis of the eye, the center of the pupil of the eye, and the corneal vertex (e.g., in memory 206 shown in FIG. 6).

In some embodiments, method 1000 includes (1024) transferring the information indicating the one or more aberrations of the eye in conjunction with the information indicating the one or more of the visual axis of the eye, the center of the pupil of the eye, and the corneal vertex (e.g., using communication interface 204 shown in FIG. 6). In some embodiments, transferring the information indicating the one or more aberrations of the eye includes transferring information representing light received by an image sensor of a wavefront sensor (e.g., an image collected by the image sensor of the waevfront sensor). In some embodiments, transferring the information indicating the one or more aberrations of the eye includes transferring information the information indicating the one or more aberrations of the eye without transferring information representing light received by an image sensor of a wavefront sensor. In some embodiments, transferring the information indicating the one or more of the visual axis of the eye, the center of the pupil of the eye, and the corneal vertex includes transferring information representing an image of the eye. In some embodiments, transferring the information indicating the one or more of the visual axis of the eye, the center of the pupil of the eye, and the corneal vertex includes transferring indicating coordinates of the visual axis of the eye.

It should be understood that the particular order in which the operations in FIG. 10 have been described is merely exemplary and is not intended to indicate that the described order is the only order in which the operations could be performed. One of ordinary skill in the art would recognize various ways to reorder the operations described herein. For example, the information indicating the one or more aberrations of the eye may be obtained after obtaining the information indicating one or more of the one or more of the visual axis of the eye, the center of the pupil of the eye, and the corneal vertex. The information indicating the position and/or the orientation of the contact lens relative to the eye may be obtained before or after obtaining the information indicating the one or more aberrations of the eye. Similarly, the information indicating the position and/or the orientation of the contact lens relative to the eye may be obtained before or after obtaining the information indicating one or more of the one or more of the visual axis of the eye, the center of the pupil of the eye, and the corneal vertex. Additionally, it should be noted that details of other processes described herein with respect to method 700, method 800, method 900, and method 1100 are also applicable in an analogous manner to method 1000 described herein with respect to FIG. 10. For brevity, these details are not repeated here.

Figure 11:
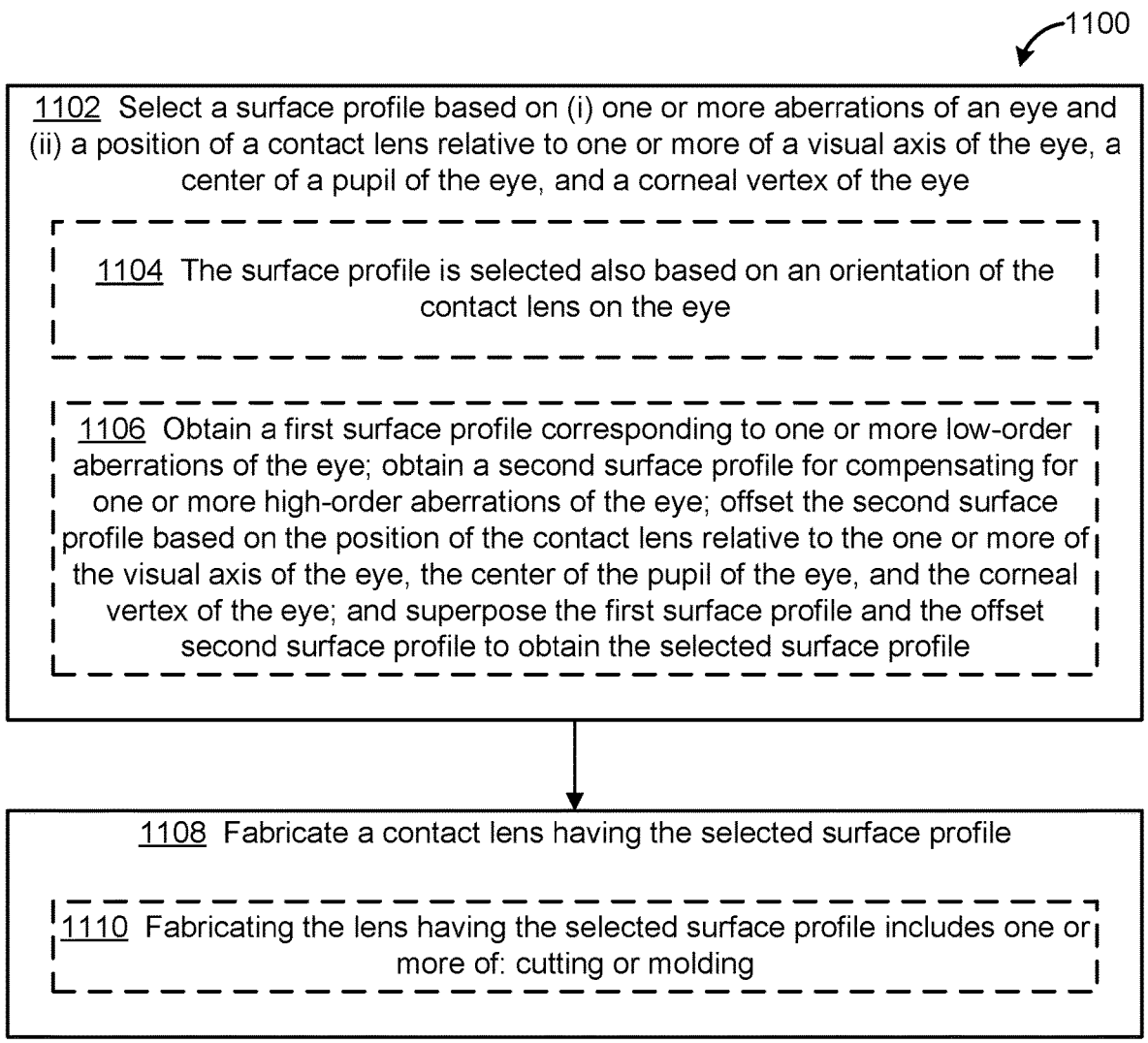
FIG. 11 is a flow chart representing a method of making a corrective lens in accordance with some embodiments.

FIG. 11 is a flow chart representing method 1100 of making a corrective lens in accordance with some embodiments.

Method 1100 for making a personalized contact lens includes (1102) selecting a surface profile based on (i) one or more aberrations of an eye and (ii) a position of a contact lens relative to one or more of a visual axis of the eye, a center of a pupil of the eye, and a corneal vertex of the eye. As shown in FIG. 1M, the surface profile for correcting high-order aberrations is offset by a distance from the center of the contact lens to the visual axis of the eye so that the high-order aberrations of the eye can be effectively compensated for by the contact lens. In addition, as shown in FIG. 1G, a center of a contact lens is not necessarily located on the visual axis of the eye. In some embodiments, the optical zone 182-3 of the contact lens 180-3 is placed based on the position of the contact lens relative to the visual axis of the eye as shown in FIG. 1J so that the optical zone 182-3 is located over the visual axis of the eye (e.g., a center of the optical zone 182-3 is located on the visual axis of the eye) when the contact lens 180-3 is placed on the eye, which can be more effective in correcting high-order aberrations. In some embodiments, the surface profile is selected based on only one of: the visual axis of the eye, the center of the pupil of the eye, or the corneal vertex of the eye (e.g., the surface profile is selected based on the visual axis of the eye without reference to the center of the pupil of the eye or the corneal vertex of the eye). In some embodiments, the surface profile is selected based on two of: the visual axis of the eye, the center of the pupil of the eye, or the corneal vertex of the eye (e.g., based on a median point between the visual axis of the eye and the center of the pupil of the eye or based on a median point between the visual axis of the eye and the corneal vertex of the eye). In some embodiments, the surface profile is selected based on all three of the visual axis of the eye, the center of the pupil of the eye, or the corneal vertex of the eye (e.g., a centroid of the visual axis of the eye, the center of the pupil of the eye, or the corneal vertex of the eye). In some embodiments, the surface profile is selected based on a point located within a triangular area defined by the visual axis of the eye, the center of the pupil of the eye, or the corneal vertex of the eye.

In some embodiments, the surface profile is selected (1104) also based on an orientation of the contact lens on the eye. For example, as shown in FIGS. 1O-1R, the surface profile is modified to place the optical zone 182 at a particular location and in a particular orientation. This allows the optical zone 182 to be positioned at a location and in an orientation suitable for a wearer's eye once the contact lens 184 is placed on the wearer's eye.

In some embodiments, method 1100 includes (1106) obtaining a first surface profile corresponding to one or more low-order aberrations of the eye; obtaining a second surface profile for compensating for one or more high-order aberrations of the eye; offsetting the second surface profile based on the position of the contact lens relative to the one or more of the visual axis of the eye, the center of the pupil of the eye, and the corneal vertex of the eye (e.g., so that the second surface profile for compensating for one or more high-order aberrations of the eye is centered around the one or more of the visual axis of the eye, the center of the pupil of the eye, and the corneal vertex of the eye); and superposing the first surface profile and the offset second surface profile to obtain the selected surface profile. For example, as shown in FIGS. 1K-1M, a surface profile of a conventional contact lens 180 (e.g., a surface profile configured to compensate for near-sightedness or farsightedness, such as a simple positive lens or a simple negative lens) is obtained, and the surface profile 188 for compensating for high-order aberrations is obtained. Then, the surface profile 188 is offset and superposed with a surface profile of contact lens 180 to obtain a combined surface profile for fabricating a contact lens.

Method 1100 also includes (1108) fabricating a contact lens having the selected surface profile. For example, a contact lens is cut to have the selected surface profile. Alternatively, the contact lens is molded to have the selected surface profile. In some embodiments, fabricating the contact lens having the selected surface profile includes (1110) one or more of: cutting or molding.

It should be noted that details of other processes described herein with respect to method 700, method 800, method 900, and method 1000 are also applicable in an analogous manner to method 1100 described herein with respect to FIG. 11. For brevity, these details are not repeated here.

In accordance with some embodiments, a contact lens made by method 1100 has a first region (e.g., an optical zone) and a second region (e.g., a region surrounding the first region) where the first region has a surface profile for correcting high-order aberrations. In some embodiments, the first region is offset from the center of the contact lens. In some embodiments, the surface profile of the first region is offset from the center of the contact lens so that the center of the surface profile aligns with a visual axis of the eye when the contact lens is positioned on the eye. In some embodiments, the first region is located over the center of the contact lens (e.g., a center of the first region corresponds to the center of the contact lens).

In some embodiments, the contact lens includes one or more features for reducing rotation and lateral movement of the contact lens while the contact lens remains on the eye. Such features are well known to a person having ordinary skill in the art and thus are omitted for brevity herein.

In some embodiments, the contact lens is a multifocal lens (e.g., FIGS. 1S-1U). The multifocal lens has (e.g., within the optical zone) a first sub-region configured to provide a first optical power (e.g., for viewing far objects) and a second sub-region configured to provide a second optical power that is different from the first optical power (e.g., for viewing near objects). In some embodiments, the multifocal lens has (e.g., within the optical zone) three or more sub-regions configured to provide different optical powers (e.g., three sub-regions, four sub-regions, five sub-regions, etc.). In some embodiments, one or more sub-regions are discrete (e.g., one sub-region and an adjacent sub-region have distinct optical powers). In some embodiments, two or more sub-regions provide continuously varying or pseudo-continuously varying optical powers (e.g., two adjacent sub-regions have optical powers for viewing near objects while two sub-regions on opposite ends of the lens or two sub-regions respectively located in a center and a periphery of the lens have distinct optical powers so that one of the two sub-regions provides an optical power for viewing near objects and the other sub-region provides an optical power for viewing far objects).

In light of these principles, we turn to certain embodiments.

In accordance with some embodiments, an optical device includes an aberrometer (e.g., a wave front sensor); a first light source for providing first light toward an eye; a lens assembly for collecting light from the eye; and a first image sensor for receiving light that has been transmitted through the lens assembly.

In some embodiments, the aberrometer is configured to determine aberrations of the eye, including high-order aberrations of the eye.

In some embodiments, the light source includes a plate with a window and a plurality of light emitting elements arranged on the plate (e.g., second light source 154 shown in FIGS. 2A (cross-sectional view) and 2G (front elevational view)). The aberrometer is positioned to measure one or more aberrations of the eye through the window of the plate; and the lens assembly and the first image sensor are positioned to collect an image of the eye through the window of the plate.

In some embodiments, the aberrometer comprises one or more of: a wavefront sensor, a corneal topographer, an optical coherence tomographer, an interferometer, a wavefront curvature sensor, a Foucault knife-edge tester, a Ronchi tester, and a phase-shifting Schlieren tester.

In some embodiments, the aberrometer is a wavefront sensor that includes: a second light source configured to emit second light and transfer the second light toward the eye; the lens assembly; an array of lenses that is distinct and separate from the lens assembly, the array of lenses configured to focus light transmitted through the lens assembly; and a second image sensor for receiving light transmitted through the lens assembly and the array of lenses.

In some embodiments, the optical device includes one or more processors; and memory storing one or more programs for execution by the one or more processors. The one or more programs include instructions for: determining one or more aberrations of the eye based on information corresponding to light received by the aberrometer; and determining a visual axis of the eye based on information corresponding to the light received by the first image sensor.

In some embodiments, the one or more programs include instructions for determining a position of a contact lens relative to the eye from information corresponding to the light received by the second image sensor while the contact lens is positioned adjacent to the eye.

In some embodiments, the one or more programs include instructions for determining an orientation of a contact lens relative to the eye from information corresponding to the light received by the second image sensor while the contact lens is positioned adjacent to the eye.

In some embodiments, the one or more programs include instructions for: storing the information corresponding to the light received by the aberrometer; and storing the information corresponding to the light received by the first image sensor.

In some embodiments, the one or more programs include instructions for: transferring the information corresponding to the light received by the aberrometer; and transferring the information corresponding to the light received by the first image sensor. By utilizing such instructions, the optical device transfers the information corresponding to the light received by the aberrometer and the information corresponding to the light received by the first image sensor to a computing device (e.g., a computer that is separate from the optical device) so that the computing device can determine one or more of: one or more aberrations of the eye based on information corresponding to light received by the aberrometer; a visual axis of the eye based on information corresponding to the light received by the first image sensor; and a position of a contact lens relative to the eye from information corresponding to the light received by the second image sensor while the contact lens is positioned adjacent to the eye.

In some embodiments, the one or more programs include instructions for determining an orientation of a contact lens relative to the eye from information corresponding to the light received by the second image sensor while the contact lens is positioned adjacent to the eye.

In some embodiments, the optical device includes a target for presenting an image of the target to the eye.

In accordance with some embodiments, a contact lens includes a first region corresponding a first optical power; and a second region corresponding a second optical power that is different from the first optical power. For example, the contact lens is a multifocal lens.

In some embodiments, the second region encircles the first region.

In accordance with some embodiments, a method for making a personalized multifocal lens includes selecting a surface profile based on one or more aberrations of an eye, wherein the one or more aberrations of the eye includes one or more high-order aberrations of the eye; and fabricating a contact lens having the selected surface profile.

The foregoing description, for purpose of explanation, has been described with reference to specific embodiments. However, the illustrative discussions above are not intended to be exhaustive or to limit the scope of claims to the precise forms disclosed. Many modifications and variations are possible in view of the above teachings. For example, the methods described above may be used for designing and making lenses for spectacles (e.g., eyeglasses). The embodiments were chosen and described in order to best explain the principles of the various described embodiments and their practical applications, to thereby enable others skilled in the art to best utilize the invention and the various described embodiments with various modifications as are suited to the particular use contemplated.

What is claimed is:

1. A method for making a personalized contact lens, the method comprising:
    selecting a surface profile based on (i) one or more aberrations of an eye and (ii) a position of a contact lens relative to one or more of a visual axis of the eye, a center of a pupil of the eye, and a corneal vertex of the eye, including:
        obtaining a first surface profile corresponding to one or more low-order aberrations of the eye;
        obtaining a second surface profile for compensating for one or more high-order aberrations of the eye;
        offsetting the second surface profile based on the position of the contact lens relative to the one or more of the visual axis of the eye, the center of the pupil of the eye, and the corneal vertex of the eye; and
        superposing the first surface profile and the offset second surface profile to obtain the selected surface profile; and
    fabricating a contact lens having the selected surface profile.

* * * * *